United States Patent
Hiroi et al.

(10) Patent No.: US 11,345,827 B2
(45) Date of Patent: *May 31, 2022

(54) ION COMPLEX MATERIAL HAVING FUNCTION OF INHIBITING ADHESION OF BIOLOGICAL SUBSTANCE AND METHOD FOR MANUFACTURING THE SAME

(71) Applicant: NISSAN CHEMICAL INDUSTRIES, LTD., Tokyo (JP)

(72) Inventors: Yoshiomi Hiroi, Toyama (JP); Ayako Otani, Shiraoka (JP); Takahiro Kishioka, Toyama (JP); Taito Nishino, Shiraoka (JP); Tomoyuki Ozawa, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/896,623

(22) PCT Filed: Jun. 9, 2014

(86) PCT No.: PCT/JP2014/065248
§ 371 (c)(1),
(2) Date: Dec. 7, 2015

(87) PCT Pub. No.: WO2014/196650
PCT Pub. Date: Dec. 11, 2014

(65) Prior Publication Data
US 2016/0122576 A1 May 5, 2016

(30) Foreign Application Priority Data

Jun. 7, 2013 (JP) .............................. JP2013-121111
Aug. 12, 2013 (JP) ................................ 2013-167774

(51) Int. Cl.
| | | |
|---|---|---|
| *C09D 133/14* | (2006.01) | |
| *C09D 143/02* | (2006.01) | |
| *C08L 101/02* | (2006.01) | |
| *C09D 201/02* | (2006.01) | |
| *C08L 43/02* | (2006.01) | |
| *C09D 5/16* | (2006.01) | |
| *C08F 230/02* | (2006.01) | |
| *C12M 1/00* | (2006.01) | |

(52) U.S. Cl.
CPC .......... *C09D 133/14* (2013.01); *C08F 230/02* (2013.01); *C08L 43/02* (2013.01); *C08L 101/02* (2013.01); *C09D 5/16* (2013.01); *C09D 143/02* (2013.01); *C09D 201/02* (2013.01); *C12M 23/20* (2013.01)

(58) Field of Classification Search
CPC .... C08F 230/02; C08F 220/34; C08L 101/02; C08L 43/02; C09D 133/14; C09D 143/02; C09D 201/02; C09D 5/16; C12M 23/20
See application file for complete search history.

(56) References Cited

U.S. PATENT DOCUMENTS 9,528,023 B2 * 12/2016 Bohling ............... C09D 133/12
2002/0000403 A1    1/2002 Tanaka et al.
(Continued)

FOREIGN PATENT DOCUMENTS

| EP | 0567886 A2 | 11/1993 |
|---|---|---|
| JP | S53-016042 A | 2/1978 |
| JP | S53-077292 A | 7/1978 |
| JP | S54-024945 A | 2/1979 |
| JP | S56-127671 A | 10/1981 |

(Continued)

OTHER PUBLICATIONS

JP 2007063459 A, Mar. 2007, Machine translation.*
JP 05156204 A, Jun. 1993, Machine translation.*
JP 07109394 A, Apr. 1995, Machine translation.*
JP-2001279164-A, Oct. 2001, Derwent Ab. (Year: 2001).*
JP-2014237731-A, Dec. 2014, machine translation (Year: 2014).*
(Continued)

*Primary Examiner* — Satya B Sastri
(74) *Attorney, Agent, or Firm* — Leydig, Voit & Mayer, Ltd.

(57) ABSTRACT

This is to provide a coating film having a function of inhibiting adhesion of a biological substance, a method for manufacturing the coating film, a copolymer obtainable by polymerizing a specific monomer mixture, a composition for forming a coating film having a specific composition, a method for manufacturing a varnish containing a copolymer to be used as a raw material of the composition for forming a coating film which is used for forming said film, and a sol for forming the coating film. In particular, this is to provide a coating film obtained by the method comprising a process of applying a composition for forming a coating film which comprises a copolymer comprising a recurring unit containing an organic group of the formula (a) and a recurring unit containing an organic group of the formula (b) and a solvent onto a substrate; and a process of drying at a temperature of −200° C. to 200° C. (wherein $U^{a1}$, $U^{a2}$, $U^{b1}$, $U^{b2}$ and $U^{b3}$, and $An^-$ are as defined in the present specification and the claims).

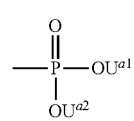

(a)

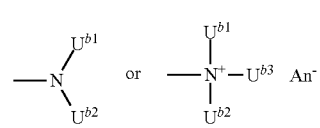

(b)

13 Claims, No Drawings

(56) References Cited

U.S. PATENT DOCUMENTS

| | | | | |
|---|---|---|---|---|
| 2004/0180146 | A1* | 9/2004 | Saikawa | B05D 7/52 427/407.1 |
| 2005/0181225 | A1* | 8/2005 | Destarac | C08F 293/005 428/544 |
| 2007/0173549 | A1* | 7/2007 | Kanzaki | B01D 71/40 521/27 |
| 2010/0193745 | A1* | 8/2010 | Harada | C08K 5/5317 252/500 |
| 2014/0194566 | A1* | 7/2014 | Auld | C08G 65/3322 524/521 |
| 2016/0115435 | A1* | 4/2016 | Otani | C08L 43/02 435/369 |
| 2017/0349777 | A1* | 12/2017 | Hiroi | C08F 230/02 |
| 2018/0305652 | A1* | 10/2018 | Katayama | C12M 1/00 |
| 2019/0218413 | A1* | 7/2019 | Hiroi | B05D 3/00 |
| 2019/0233792 | A1* | 8/2019 | Hiroi | C12M 3/00 |

FOREIGN PATENT DOCUMENTS

| | | | | |
|---|---|---|---|---|
| JP | S59-084964 | A | | 5/1984 |
| JP | H01-266126 | A | | 10/1989 |
| JP | 05156204 | A | * | 6/1993 |
| JP | H05-156204 | A | | 6/1993 |
| JP | H06-092979 | A | | 4/1994 |
| JP | 07109394 | A | * | 4/1995 |
| JP | H07-109394 | A | | 4/1995 |
| JP | 2001-279164 | A | | 10/2001 |
| JP | 2001279164 | A | * | 10/2001 ............ B82Y 30/00 |
| JP | 2001-323030 | A | | 11/2001 |
| JP | 2005-239560 | A | | 9/2005 |
| JP | 2006-076973 | A | | 3/2006 |
| JP | 2007-063459 | A | | 3/2007 |
| JP | 2007063459 | A | * | 3/2007 |
| JP | 2007-231174 | A | | 9/2007 |
| JP | 2008-239869 | A | | 10/2008 |
| JP | 2009-143865 | A | | 7/2009 |
| JP | 2010-233999 | A | | 10/2010 |
| JP | 2014237731 | A | * | 12/2014 ............ B82Y 30/00 |
| WO | WO 1999/049338 | A1 | | 9/1999 |
| WO | WO-2012166691 | A1 | * | 12/2012 ............ C09D 7/62 |
| WO | WO 2013/047385 | A1 | | 4/2013 |

OTHER PUBLICATIONS

Sakiyama et al., "Transition and Prospect of Hemodialysis Membrane," *Japanese Journal of Artificial Organs*, 39(1): 77-80 (2010).
Takai et al., "Functional Biointerface for Microfluidic Devices Using Phospholipid Polymers," *Japanese Journal of Polymer Science and Technology*, 65(3): 228-235 (2008).
Japanese Patent Office, International Search Report in International Patent Application No. PCT/JP2014/065248 (dated Sep. 16, 2014).
Japanese Patent Office, Notice of Reasons for Refusal in Japanese Patent Application No. 2019-024332 (dated Mar. 3, 2020).

* cited by examiner

ION COMPLEX MATERIAL HAVING FUNCTION OF INHIBITING ADHESION OF BIOLOGICAL SUBSTANCE AND METHOD FOR MANUFACTURING THE SAME

CROSS-REFERENCE TO RELATED APPLICATIONS

This patent application is the U.S. national phase of International Patent Application No. PCT/JP2014/065248, filed Jun. 9, 2014, which claims the benefit of Japanese Patent Application No. 2013-167774, filed on Aug. 12, 2013, and Japanese Patent Application No. 2013-121111, filed on Jun. 7, 2013, which are incorporated by reference in their entireties herein.

TECHNICAL FIELD

The present invention relates to an ion complex material having a function of inhibiting adhesion of a biological substance and a method for manufacturing the same. The present invention specifically relates to a coating film having a function of inhibiting adhesion of a biological substance, a method for manufacturing the coating film, a copolymer obtainable by polymerizing a specific monomer mixture, a composition for forming a coating film having a specific composition, a method for producing a varnish containing a copolymer to be used as a raw material of the composition for forming a coating film which is used for forming said film, and a sol for forming the coating film.

BACKGROUND ART

For suppressing adhesion of a biological substance to medical instruments, equipments, etc., such as an artificial dialyzer, artificial organs, medical equipments, etc., various coating materials having a function of inhibiting adhesion of a biological substance have been proposed. Among these, it has been known a material of inhibiting adhesion of a biological substance by coating a polymer having an ethylene glycol chain at the side chain and, for example, in Patent Document 1, an example of coating a copolymer of 2-methoxyethyl acrylate onto nonwoven fabric such as a blood filter and a dialysis filter, etc., has been disclosed. Also, in Non-Patent Document 1, to impart a function of inhibiting adhesion of a biological substance to polysulfone (PSF) or polyether sulfone (PES), etc., which is used as a substrate for an artificial dialysis film, it has been disclosed that polyvinylpyrrolidone (PVP) having a hydrophilic property is coated. However, whereas these materials have a function of inhibiting adhesion of a biological substance which is expected by having the effect of the hydrophilic property, etc., solubility of the polymer itself to water is suppressed and solubility in an alcohol or an organic solvent is heightened, elution of the coating film itself has been identified by the causes of washing with ethanol, etc., for sterilization, shear stress (shearing stress) to the coating film by a high viscosity biological substance, etc., and use for a long period of time, etc., and yet allergy, etc., due to the eluate is a matter of concern.

On the other hand, a material having a polymer material containing a cation and an anion at the side chain on the surface thereof has been known to have a function of preventing adhesion of a biological substance (protein, cell, etc.) by being maintained to electrically neutral at the surface thereof due to electrostatic balance. In addition, it has been proposed a coating material using such a function, and various reports have been made on the fixation or immobilization method to glass or a polymer substrate, etc. For example, in Non-Patent Document 2, it has been reported that surface modification was accomplished by chemical adhesion with a glass substrate using a polymer obtained by copolymerizing 2-methacryloyloxyethyl phosphorylcholine (MPC) having a similar molecular structure to a phospholipid as a charge neutralization unit and 3-(trimethoxysilyl)propyl methacrylate having a silane coupling group. On the other hand, it has also been reported that onto a polymer substrate, a polymer into which butyl methacrylate has been copolymerized is to be fixed onto the substrate by aiming physical adhesion due to hydrophobic interaction. However, according to these methods, it is necessary to select a kind of the polymer depending on a kind of the substrate.

Also, in Patent Document 2, a coating film which is obtained from a film formed from a coating solution containing a polymer having a phosphoric acid ester group by subjecting to heat treatment at 200 to 450° C. has been disclosed. To suppress elution of the coating film into an aqueous medium, it is necessary to carry out heat treatment at a high temperature of 200 to 450° C. after coating onto a substrate, so that a heating device such as an oven, a hot plate, etc., is necessary for the heat treatment. In addition, there was a problem that it can be difficultly applied to a substrate having low heat resistance such as a resin material, etc. Further, various polymers have been polymerized to manufacture a coating solution for forming a coating film, but in the Examples, polymerization reaction was carried out in ethanol, and polymerization reactivity in water was unclear.

Further, in Patent Document 3, there are disclosed a novel acrylic phosphoric acid ester amine salt monomer (half salt) obtained by reacting an amine with an acrylic acidic phosphoric acid ester monomer in the presence of water to selectively proceed an acid-base reaction and a method for manufacturing the same. The amine salt (half salt) has been disclosed to have a wide range of uses and usefulness in the field of a photosensitive resin as a monomer for providing rubber elasticity or a modifier of an oil-soluble substance, but it is unclear about polymerization reactivity of the amine salt (half salt) monomer itself in water, and a function of inhibiting adhesion of the obtained polymer to a biological substance. In addition, a used ratio of the above-mentioned acrylic acidic phosphoric acid ester monomer in the whole used monomer at the time of polymerization in a polar solvent such as methanol, etc., is mainly around 5% to around 1% in many examples, and there is disclosed that if an amount is larger, the product is gelled.

Moreover, in Patent Document 4, a blood purifier having a hollow fiber film containing polyvinylpyrrolidone (PVP) has been disclosed, a mode diameter at the peak which is residing at the largest diameter in the particle diameter distribution measured by the dynamic light scattering method of the PVP in the hollow fiber is disclosed to be 300 nm or less, and to coat the inside of the hollow fiber using the PVP coating liquid has been disclosed.

PRIOR ART DOCUMENTS

Patent Documents

Patent Document 1: JP 2001-323030A
Patent Document 2: JP 2007-63459A
Patent Document 3: JP Hei.6-92979A
Patent Document 4: JP 2010-233999A

Non-Patent Documents

Non-Patent Document 1: The Japanese Journal of Artificial Organs, Vol. 39, No. 1, pp. 77 (2010)

Non-Patent Document 2: Japanese Journal of Polymer Science and Technology, Vol. 65, No. 3, pp. 228 (2008)

SUMMARY OF THE INVENTION

Problems to be Solved by the Invention

The present invention has been done to overcome the three problems as mentioned below: (1) a coating film obtainable by a heat treatment at high temperature of 200 to 450° C. is required to suppress elution thereof into an aqueous medium, (2) a material of the coating film is required to be suitably selected depending on the kind of the substrate, and (3) a copolymer to be used in the above-mentioned composition for forming a coating film is easily gelled at the time of manufacturing a varnish, and, in particular, to provide a coating film having a function of inhibiting adhesion of a biological substance which can be easily formed only by a low temperature drying process, a method for manufacturing the coating film, a copolymer obtainable by polymerizing a specific monomer mixture, a composition for forming a coating film having a specific composition, a method for producing a varnish containing a copolymer to be used as a raw material of the composition for forming a coating film which is used for forming said film, and a sol for forming the coating film.

Means for Solving the Problems

The present inventions relate to, as the first aspect, a coating film obtained by a method comprising a process of applying a composition for forming a coating film which comprises a copolymer comprising a recurring unit containing an organic group of the following formula (a) and a recurring unit containing an organic group of the following formula (b):

$$\begin{array}{c} O \\ \| \\ -P-OU^{a1} \\ | \\ OU^{a2} \end{array} \quad (a)$$

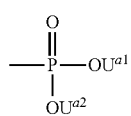

(wherein $U^{a1}$, $U^{a2}$, $U^{b1}$, $U^{b2}$ and $U^{b3}$ each independently represent a hydrogen atom or a linear or branched alkyl group having 1 to 5 carbon atoms, An⁻ represents an anion selected from the group consisting of a halide ion, an inorganic acid ion, a hydroxide ion and an isothiocyanate ion) and a solvent onto a substrate; and a process of drying at a temperature of −200° C. to 200° C., as the second aspect, the coating film described in the first aspect, wherein the solvent contains water or an alcohol, as the third aspect, the coating film described in the first aspect or the second aspect, wherein a concentration of the copolymer in the composition for forming a coating film is 0.01% by mass to 4% by mass, as the fourth aspect, the coating film described in any one of the first aspect to the third aspect, wherein the substrate is selected from the group consisting of glass, a metal containing compound, a semi-metal containing compound and a resin, as the fifth aspect, the coating film described in any one of the first aspect to the fourth aspect, wherein the film has a function of inhibiting adhesion of a biological substance, as the sixth aspect, the coating film described in any one of the first aspect to the fifth aspect, wherein the copolymer contains recurring units of the following formula (a1) and the formula (b1):

$$\begin{array}{c} T^a \\ | \\ -(CH_2C)- \\ | \\ Q^a-(R^a-O)_m-P-OU^{a1} \\ | \\ OU^{a2} \end{array} \quad (a1)$$

$$\begin{array}{cc} T^b & T^b \\ | & | \\ -(CH_2C)- & -(CH_2C)- \\ | \quad U^{b1} & | \quad U^{b1} \\ Q^b-R^b-N & \text{or} \quad Q^b-R^b-N^+-U^{b3} \text{ An}^- \\ \quad U^{b2} & \quad U^{b2} \end{array} \quad (b1)$$

(wherein $T^a$, $T^b$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom(s), An⁻ represents an anion selected from the group consisting of a halide ion, an inorganic acid ion, a hydroxide ion and an isothiocyanate ion, and m is an integer of 0 to 6), as the seventh aspect, the coating film described in any one of the first aspect to the sixth aspect, wherein m is 1, and $R^a$ and $R^b$ each independently represent an ethylene group of a propylene group, as the eighth aspect, the coating film described in any one of the first aspect to the seventh aspect, wherein the method further comprises a process of previously adjusting a pH of the composition for forming a coating film, and as the ninth aspect, the coating film described in any one of the first aspect to the eighth aspect, wherein the method further comprises a process of washing a film obtained after the process of drying with at least one solvent selected from the group consisting of water and an aqueous solution containing an electrolyte.

In addition, the present inventions relate to, as the tenth aspect, a method for manufacturing a coating film comprising a process of applying a composition for forming a coating film which comprises a copolymer comprising a recurring unit containing an organic group of the following formula (a) and a recurring unit containing an organic group of the following formula (b):

$$\begin{array}{c} O \\ \| \\ -P-OU^{a1} \\ | \\ OU^{a2} \end{array} \quad (a)$$

$$\begin{array}{cc} U^{b1} & U^{b1} \\ / & | \\ -N & \text{or} \quad -N^+-U^{b3} \text{ An}^- \\ \backslash & | \\ U^{b2} & U^{b2} \end{array} \quad (b)$$

(wherein $U^{a1}$, $U^{a2}$, $U^{b1}$, $U^{b2}$ and $U^{b3}$ each independently represent a hydrogen atom or a linear or branched alkyl group having 1 to 5 carbon atoms, An⁻ represents an anion selected from the group consisting of a halide ion, an inorganic acid ion, a hydroxide ion and an isothiocyanate ion) and a solvent onto a substrate; and a process of drying at a temperature of −200° C. to 200° C., and as the eleventh aspect, a copolymer obtained by copolymerizing a monomer mixture comprising at least compounds of the following formula (A) and the formula (B):

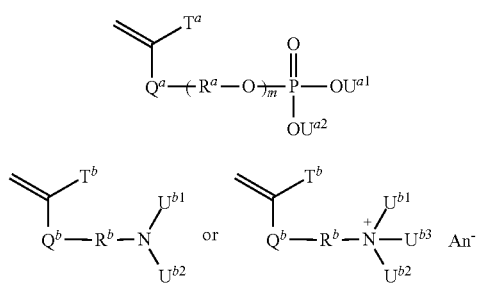

(A)

(B)

(wherein $T^a$, $T^b$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom(s), An⁻ represents an anion selected from the group consisting of a halide ion, an inorganic acid ion, a hydroxide ion and an isothiocyanate ion, and m is an integer of 0 to 6) and a compound of the following formula (C) or (D):

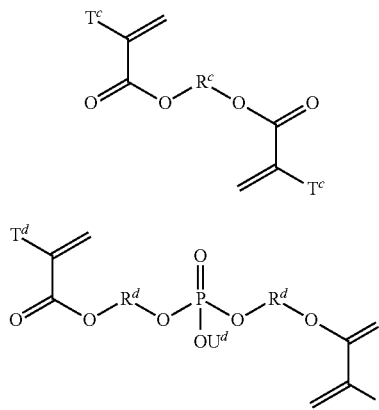

(C)

(D)

(wherein $T^c$, $T^d$ and $U^d$ each independently represent a hydrogen atom or a linear or branched alkyl group having 1 to 5 carbon atoms, $R^c$ and $R^d$ each independently represent a linear or branched alkylene group having 1 to 10 carbon atoms which may be substituted by a halogen atom(s)).

Further, the present inventions relate to, as the twelfth aspect, a composition for forming a coating film which comprises (i) a copolymer comprising a recurring unit containing an organic group of the following formula (a) and a recurring unit containing an organic group of the following formula (b):

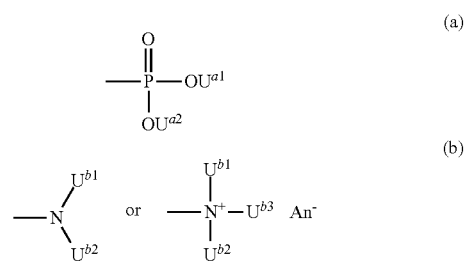

(a)

(b)

(wherein $U^{a1}$, $U^{a2}$, $U^{b1}$, $U^{b2}$ and $U^{b3}$ each independently represent a hydrogen atom or a linear or branched alkyl group having 1 to 5 carbon atoms, An⁻ represents an anion selected from the group consisting of a halide ion, an inorganic acid ion, a hydroxide ion and an isothiocyanate ion), (ii) a solvent; and (iii) a pH adjusting agent, as the thirteenth aspect, the composition described in the twelfth aspect, wherein the copolymer contains recurring units of the following formula (a1) and the formula (b1):

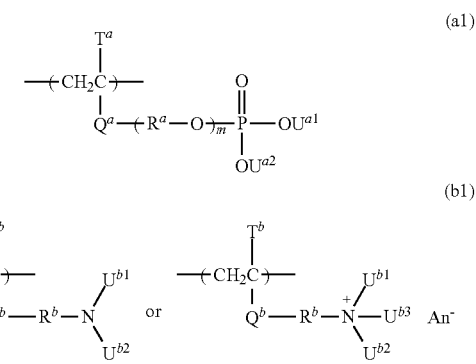

(a1)

(b1)

(wherein $T^a$, $T^b$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom(s), An⁻ represents an anion selected from the group consisting of a halide ion, an inorganic acid ion, a hydroxide ion and an isothiocyanate ion, and m is an integer of 0 to 6).

Moreover, the present inventions relate to, as the fourteenth aspect, a method for manufacturing a varnish containing a copolymer which comprises a process of reacting compounds of the following formula (A) and the formula (B):

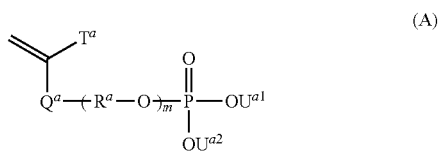

(A)

-continued

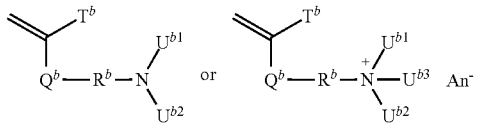
(B)

(wherein $T^a$, $T^b$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom(s), An⁻ represents an anion selected from the group consisting of a halide ion, an inorganic acid ion, a hydroxide ion and an isothiocyanate ion, and m is an integer of 0 to 6) in a solvent with a total concentration of the both compounds of 0.01% by mass to 4% by mass, as the fifteenth aspect, the manufacturing method of a varnish containing a copolymer described in the fourteenth aspect, wherein m is 1, and $R^a$ and $R^b$ each independently represent an ethylene group of a propylene group, as the sixteenth aspect, the manufacturing method of a varnish containing a copolymer described in the fourteenth aspect or the fifteenth aspect, wherein the solvent contains water or an alcohol, as the seventeenth aspect, the manufacturing method of a varnish containing a copolymer described in any one of the fourteenth aspect to the sixteenth aspect, wherein the solvent contains 10% by mass to 100% by mass of water, and as the eighteenth aspect, the manufacturing method of a varnish containing a copolymer described in any one of the fourteenth aspect to the sixteenth aspect, wherein the solvent contains 10% by mass to 100% by mass of an alcohol.

Furthermore, the present inventions relate to, as the nineteenth aspect, a method for manufacturing a varnish containing a copolymer which comprises a process of reacting a mixture containing compounds of the following formula (A) and the formula (B):

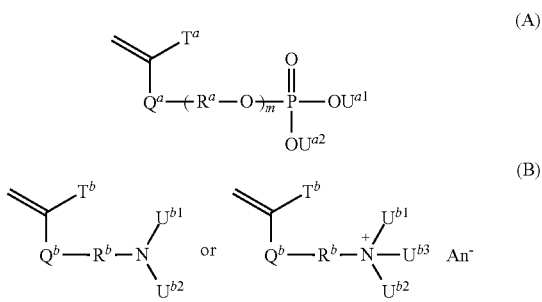

(wherein $T^a$, $T^b$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom(s), An⁻ represents an anion selected from the group consisting of a halide ion, an inorganic acid ion, a hydroxide ion and an isothiocyanate ion, and m is an integer of 0 to 6), a solvent and a polymerization initiator, by adding the mixture dropwise into a solvent maintained at a temperature higher than 10-hr half-life temperature of the polymerization initiator.

Still further, the present inventions relate to, as the twentieth aspect, a sol which comprises a copolymer comprising a recurring unit containing an organic group of the following formula (a) and a recurring unit containing an organic group of the following formula (b):

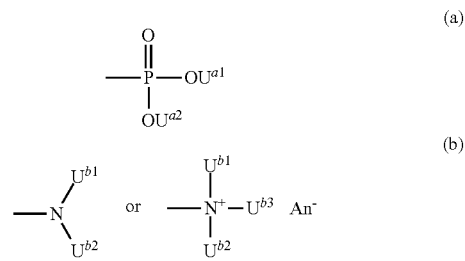

(wherein $U^{a1}$, $U^{a2}$, $U^{b1}$, $U^{b2}$ and $U^{b3}$ each independently represent a hydrogen atom or a linear or branched alkyl group having 1 to 5 carbon atoms, An⁻ represents an anion selected from the group consisting of a halide ion, an inorganic acid ion, a hydroxide ion and an isothiocyanate ion), as the twenty-first aspect, the sol described in the twelfth aspect, wherein an average particle diameter in particle diameter distribution measured by a dynamic light scattering method is 2 nm or more and 500 nm or less.

Effect of the Invention

The coating film of the present invention can be formed by applying a composition for forming a coating film containing a copolymer which contains an anion of the formula (a) and a cation of the formula (b) onto a substrate, then, subjecting to a low temperature drying (−200° C. to 200° C.) process. The coating film of the present invention can be firmly fixed without selecting a kind of the substrate such as glass, a metal containing compound, a semi-metal containing compound and a resin (a synthetic resin and a natural resin) by forming an ionic bonding (ion complex) of the anion of the formula (a) and the cation of the formula (b), and after fixation, it gives a coating film excellent in durability against an aqueous solvent (water, a phosphate buffered physiological saline (PBS), an alcohol, etc.). Also, it gives a coating film excellent in a function of inhibiting adhesion of a biological substance, since ion balance of the copolymer is controlled by previously adjusting a pH of the composition for forming a coating film with a pH adjusting agent, etc., or by washing the coating film after drying with water and/or an aqueous solution containing an electrolyte.

Further, when the copolymer contained in the composition for forming a coating film of the present invention is to be synthesized, a phosphoric acid ester group which is a side chain of the copolymer has been known, for example, as disclosed in Patent Document 3, to have strong association property so that it sometimes gelled depending on the polymerization conditions, but in the present invention, a method for manufacturing a transparent varnish containing a copolymer can be provided by controlling the total concentration of the compound for synthesizing the copolymer in the reaction solvent to 4% by mass or less, or controlling an order of addition of a reactant and a reagent, or an addition temperature without gelation. According to this method, even if a polymer containing, for example, around 50 mol % of a recurring unit having a phosphoric acid ester group in the copolymer according to the present invention is used, a transparent varnish containing a copolymer can be manufactured without gelation. The varnish containing a copolymer can be used as a composition for forming a coating film for forming the coating film of the present invention, or a raw material for preparing the same.

EMBODIMENTS TO CARRY OUT THE INVENTION

The coating film of the present invention is a coating film obtained by a method comprising a process of applying a composition for forming a coating film containing a copolymer which contains a recurring unit containing an organic group of the following formula (a) and a recurring unit containing an organic group of the following formula (b):

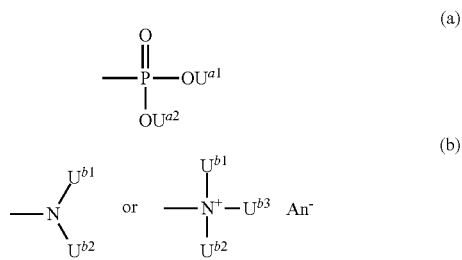

(wherein $U^{a1}$, $U^{a2}$, $U^{b1}$, $U^{b2}$ and $U^{b3}$ each represent a hydrogen atom or a linear or branched alkyl group having 1 to 5 carbon atoms, An⁻ represents an anion selected from the group consisting of a halide ion, an inorganic acid ion, a hydroxide ion and an isothiocyanate ion) and a solvent onto a substrate, and a process of drying at a temperature of −200° C. to 200° C.

The copolymer according to the present invention is not particularly limited so long as it is a copolymer which contains a recurring unit containing an organic group of the above-mentioned formula (a), and a recurring unit containing an organic group of the above-mentioned formula (b). The copolymer is desirably a material obtained by subjecting a monomer containing an organic group of the above-mentioned formula (a) and a monomer containing an organic group of the above-mentioned formula (b) to radical polymerization, and a material obtained by polycondensation or polyaddition reaction may be used. Examples of the copolymer include a vinyl polymerized polymer in which an olefin is reacted, a polyamide, a polyester, a polycarbonate, a polyurethane, and among these, a vinyl polymerized polymer in which an olefin is reacted or a (meth)acrylic polymer in which a (meth)acrylate compound is polymerized is desired. Further, in the present invention, the (meth) acrylate compound means both of an acrylate compound and a methacrylate compound. For example, a (meth)acrylic acid means an acrylic acid and a methacrylic acid.

In the present invention, "a halide ion" means a fluoride ion, a chloride ion, a bromide ion or an iodide ion.

In the present invention, "an inorganic acid ion" means a carbonate ion, a sulfate ion, a phosphate ion, a hydrogen phosphate ion, a dihydrogen phosphate ion, a nitrate ion, a perchlorate ion or a borate ion.

As the above-mentioned An⁻, preferred are a halide ion, a sulfate ion, a phosphate ion, a hydroxide ion and an isothiocyanate ion, and particularly preferred is a halide ion.

In the present invention, "a linear or branched alkyl group having 1 to 5 carbon atoms" may be mentioned, for example, a methyl group, an ethyl group, an n-propyl group, an isopropyl group, an n-butyl group, an isobutyl group, a s-butyl group, a t-butyl group, a n-pentyl group, a 1-methylbutyl group, a 2-methylbutyl group, a 3-methylbutyl group, a 1,1-dimethylpropyl group, a 1,2-dimethylpropyl group, a 2,2-dimethylpropyl group or a 1-ethylpropyl group. As $U^{a1}$, $U^{a2}$, $U^{b1}$, $U^{b2}$ and $U^{b3}$, preferred may be mentioned a hydrogen atom, a methyl group or an ethyl group, $U^{a1}$ and $U^{a2}$ of the formula (a) are more preferably hydrogen atoms, and $U^{b1}$, $U^{b2}$ and $U^{b3}$ of the formula (b) are more preferably methyl groups.

A ratio of the recurring unit containing an organic group of the formula (a) in the copolymer according to the present invention is 20 mol % to 80 mol %, preferably 30 mol % to 70 mol %, more preferably 40 mol % to 60 mol %. Further, the copolymer according to the present invention may contain two or more kinds of the recurring units containing an organic group of the formula (a).

A ratio of the recurring unit containing an organic group of the formula (b) in the copolymer according to the present invention may be the whole remainder subtracting the ratio of the above-mentioned formula (a) from the whole of the copolymer, or may be the remainder subtracting the total ratio of the above-mentioned formula (a) and a third component mentioned below from the same. Further, the copolymer according to the present invention may contain two or more kinds of the recurring units containing an organic group of the formula (b).

The solvent to be contained in the composition for forming a coating film of the present invention may be mentioned water, a phosphate buffered physiological saline (PBS) and an alcohol. Examples of the alcohol include an alcohol having 2 to 6 carbon atoms, such as, ethanol, propanol, isopropanol, 1-butanol, 2-butanol, isobutanol, t-butanol, 1-pentanol, 2-pentanol, 3-pentanol, 1-heptanol, 2-heptanol, 2,2-dimethyl-1-propanol (neopentyl alcohol), 2-methyl-1-propanol, 2-methyl-1-butanol, 2-methyl-2-butanol (t-amyl alcohol), 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol and cyclohexanol. The solvent may be used alone or a mixed solvent of these combinations, and in the viewpoint of dissolution of the copolymer, it is preferably selected from water, PBS and ethanol.

A concentration of the solid component in the composition for forming a coating film according to the present invention is desirably 0.01 to 50% by mass to form a coating film uniformly. Also, the concentration of the copolymer in the composition for forming a coating film is preferably 0.01 to 4% by mass, more preferably 0.01 to 3% by mass, particularly preferably 0.01 to 2% by mass, more preferably 0.01 to 1% by mass. If the concentration of the copolymer is 0.01% by mass or less, the concentration of the copolymer of the obtainable composition for forming a coating film is too low so that a coating film having a sufficient film thickness cannot be formed, while if it is 4% by mass or more, storage stability of the composition for forming a coating film is poor, and there is a possibility of causing deposition of the dissolved material or gelation thereof.

Further, to the composition for forming a coating film of the present invention may be added other substances within the range which does not impair the performance of the obtainable coating film depending on the necessity, in addition to the above-mentioned copolymer and the solvent. The other substances may be mentioned an antiseptic, a surfactant, a primer which heighten adhesiveness with the substrate, an antifungal agent and a saccharide, etc.

To control ion balance of the copolymer in the composition for forming a coating film according to the present invention, when the coating film of the present invention is to be obtained, a process of previously adjusting a pH of the composition for forming a coating film may be contained. The pH adjustment may be carried out, for example, by adding a pH adjusting agent to the composition containing the above-mentioned copolymer and a solvent, to make the pH of the composition 3.5 to 8.5, more preferably 4.0 to 8.0. A kind of the pH adjusting agent which can be used and an amount thereof are appropriately selected depending on the concentration of the above-mentioned copolymer, and an existing ratio of the anion and the cation, etc. Examples of the pH adjusting agent include an organic amine such as ammonia, diethanolamine, pyridine, N-methyl-D-glucamine, tris(hydroxymethyl)aminomethane; an alkali metal hydroxide such as potassium hydroxide, sodium hydroxide; an alkali metal halide such as potassium chloride, sodium chloride; an inorganic acid such as sulfuric acid, phosphoric acid, hydrochloric acid, carbonic acid or an alkali metal salt thereof; a quaternary ammonium cation such as choline or a mixture thereof (for example, a buffer such as a phosphate buffered physiological saline). Among these, ammonia, diethanolamine, sodium hydroxide, choline, N-methyl-D-glucamine and tris(hydroxymethyl)aminomethane are preferred, and ammonia, diethanolamine, sodium hydroxide and choline are particularly preferred.

Accordingly, the present invention relates to the composition for forming a coating film comprising (i) the copolymer containing the above-mentioned recurring unit containing an organic group of the formula (a) and the above-mentioned recurring unit containing an organic group of the formula (b), (ii) a solvent, and (iii) a pH adjusting agent. Specific examples of the copolymer, the solvent and the pH adjusting agent are as mentioned above.

The present invention also relates to a sol comprising the copolymer which contains the above-mentioned recurring unit containing an organic group of the formula (a) and the above-mentioned recurring unit containing an organic group of the formula (b). Specific examples of the copolymer and the solvent contained in the sol are as mentioned above.

The sol of the present invention preferably further contains a pH adjusting agent. Specific examples of the pH adjusting agent are as mentioned above. The sol of the present invention is more preferably a sol for forming a coating film, and is one embodiment of the composition for forming a coating film.

The composition for forming a coating film according to the present invention is applied onto a substrate and dried to form a coating film.

The substrate for forming the coating film of the present invention may be mentioned glass, a metal containing compound or a semi-metal containing compound, activated charcoal or a resin. The metal containing compound or the semi-metal containing compound may be mentioned, for example, ceramics comprising a metal oxide as a basic component, which are a sintered body baked by a heat treatment at a high temperature, a semiconductor such as silicon, an inorganic solid material including molded product of an inorganic compound such as a metal oxide or a semimetal oxide (silicon oxide, alumina, etc.), a metal carbide or a semi-metal carbide, a metal nitride or a semi-metal nitride (silicon nitride, etc.), a metal boride or a semi-metal boride, aluminum, nickel-titanium, stainless (SUS304, SUS316, SUS316L, etc.).

The resin may be either a natural resin or a synthetic resin, and the natural resin preferably used may be mentioned cellulose, cellulose triacetate (CTA), cellulose to which dextran sulfate has been fixed, etc., while the synthetic resin preferably used may be mentioned polyacrylonitrile (PAN), polyester-based polymer alloy (PEPA), polystyrene (PS), polysulfone (PSF), polyethylene terephthalate (PET), polymethyl methacrylate (PMMA), polyvinyl alcohol (PVA), polyurethane (PU), ethylene vinyl alcohol (EVAL), polyethylene (PE), polyester (PE), polypropylene (PP), polyvinylidene fluoride (PVDF), various kinds of ion exchange resins or polyether sulfone (PES), etc. The coating film of the present invention can be formed by a low temperature drying, so that it can be applied to a resin having low heat resistance, etc.

For forming the coating film of the present invention, the above-mentioned composition for forming a coating film is applied onto at least a part of the surface of the substrate. The application method is not particularly limited, and a usual coating method such as spin coating, dip coating, a solvent casting method, etc., may be used.

The drying process of the coating film according to the present invention is carried out under the atmosphere or under vacuum at a temperature within the range of $-200°$ C. to $200°$ C. According to the drying process, the solvent in the above-mentioned composition for forming a coating film is removed, and the units of the formula (a) and the formula (b) of the copolymer according to the present invention form ionic bonding to completely fix to the substrate.

The coating film may be formed by, for example, the drying at room temperature ($10°$ C. to $35°$ C., for example, $25°$ C.), and for forming the coating film more rapidly, it may be dried at, for example, $40°$ C. to $50°$ C. In addition, a drying process at a very low temperature to low temperature ($-200°$ C. to around $-30°$ C.) by a freeze drying method may be used. Freeze drying is called as freeze vacuum drying, and is a method of removing a solvent under a vacuum state by sublimation while generally cooling a material to be dried with a coolant. A general coolant to be used in the freeze drying may be mentioned a mixed medium of dry ice and methanol ($-78°$ C.), liquid nitrogen ($-196°$ C.), etc.

If the drying temperature is $-200°$ C. or lower, a coolant which is not general must be used so that it lacks in versatility, and it takes a long time for drying due to sublimation of the solvent so that the efficiency is bad. If the drying temperature is $200°$ C. or higher, ionic bonding reaction at the surface of the coating film excessively proceeds and the surface loses a hydrophilic property, whereby a function of inhibiting adhesion of a biological substance cannot be exhibited. More preferred drying temperature is $10°$ C. to $180°$ C., and more preferred drying temperature is $25°$ C. to $150°$ C.

After the drying, to remove impurities, unreacted monomer, etc., remained on the coating film, and further to adjust ion balance of the copolymer in the film, it is desired to wash the film by washing with flowing water or washing with ultrasonic wave, etc., with one or more solvent selected from water and an aqueous solution containing an electrolyte. The above-mentioned water and the aqueous solution containing an electrolyte may be heated, for example, within the range of $40°$ C. to $95°$ C. The aqueous solution containing an electrolyte is preferably PBS, a physiological saline (a solution containing sodium chloride alone), a Dulbecco's phosphate buffered physiological saline, a Tris buffered physiological saline, a HEPES buffered physiological saline and a Veronal buffered physiological saline, and PBS is particularly preferred. After fixation, even when the coating film is washed with water, PBS and an alcohol, etc., it does not elute and is still firmly fixed to the substrate. Even when a biological substance is adhered to the formed coating film, it can be easily removed thereafter by washing, etc., and the surface of the substrate on which the coating film of the present invention has been formed has a function of inhibiting adhesion of a biological substance.

Examples of the application of the coating film according to the present invention include a coating film for a filter of an artificial dialyzer, and the coating film of the present invention has good fixing property to the synthetic resin (for example, PES, PS and PSF, etc.) used as a filter, and has good durability after fixation. A form of the substrate is not particularly limited, and may be mentioned a substrate board, fiber, particles, a gel form, a porous form, etc., a shape of which may be a flat plate or a curved surface.

For example, when a coating film for a filter of an artificial dialyzer is to be manufactured, a liquid of the composition for forming a coating film according to the present invention is flown through the inside of the filter prepared by the above-mentioned raw material, for example, having a hollow fiber shape with a diameter of 0.1 to 500 μm, thereafter, subjecting to a drying process and a washing process (hot water (for example, 40° C. to 95° C.) washing, etc.) to manufacture the film.

If necessary, there is a case where a treatment with γ ray, ethylene oxide, an autoclave, etc., is carried out for sterilization.

A film thickness of the coating film of the present invention is preferably 10 to 1,000 Å, more preferably 10 to 500 Å.

The biological substance may be mentioned a protein, a saccharide, a nucleic acid and a cell or a combination thereof. The protein may be mentioned, for example, fibrinogen, bovine serum albumin (BSA), human albumin, various kinds of globulins, β-lipoprotein, various kinds of antibodies (IgG, IgA, IgM), peroxidase, various kinds of complements, various kinds of lectins, fibronectin, lysozyme, von Willebrand factor (vWF), serum γ-globulin, pepsin, ovalbumin, insulin, histone, ribonuclease, collagen and cytochrome c, the saccharide may be mentioned, for example, glucose, galactose, mannose, fructose, heparin and hyaluronic acid, the nucleic acid may be mentioned, for example, deoxyribonucleic acid (DNA) and ribonucleic acid (RNA), the cell may be mentioned, for example, fibroblast, bone marrow cells, B lymphocytes, T lymphocytes, neutrophils, red blood cells, platelets, macrophages, monocytes, bone cells, bone marrow cells, perithelial cells, dendritic cells, keratinocytes, fat cells, mesenchymal cells, epithelial cells, epidermal cells, endothelial cells, vascular endothelial cells, hepatic parenchymal cells, cartilage cells, cumulus cells, neural cells, glial cells, neurons, oligodendrocyte, microglia, astroglial cells, heart cells, esophagus cells, muscle cells (for example, smooth muscle cells or skeletal muscle cells), pancreatic beta cells, melanocytes, hematopoietic precursor cells, mononuclear cells, embryonic stem cells (ES cell), embryonic tumor cells, embryonic germline stem cells, induced pluripotent stem cells (iPS cell), neural stem cells, hematopoietic stem cells, mesenchymal stem cells, liver stem cells, pancreatic stem cells, muscle stem cells, germline stem cells, intestinal stem cells, cancer stem cells, hair follicle stem cells, and various kinds of cell lines (for example, HCT116, Huh7, HEK293 (human embryonic kidney cell), HeLa (human cervical cancer cell lines), HepG2 (human liver cancer cell lines), UT7/TPO (human leukemia cell lines), CHO (Chinese hamster ovary cell lines), MDCK, MDBK, BHK, C-33A, HT-29, AE-1, 3D9, Ns0/1, Jurkat, NIH3T3, PC12, S2, Sf9, Sf21, High Five, Vero), etc., and the coating film of the present invention has a particularly high function of inhibiting adhesion to platelets. Also, the coating film of the present invention has a particularly high function of inhibiting adhesion against a serum in which a protein or a saccharide is mixed.

The coating film of the present invention has a function of inhibiting adhesion of a biological substance, so that it can be suitably used as a coating film for a medical substrate. It can be suitably used as, for example, a leukocyte removing filter, a blood transfusion filter, a virus-removing filter, a micro blood clots-removing filter, a module for blood purification, an artificial heart, an artificial lung, a blood circuit, an artificial blood vessel, a blood vessel bypass tube, a medical tube, an artificial valve, a cannula, a stent, a catheter, a catheter in blood vessel, a balloon catheter, a guide wire, a suture, an indwelling needle, shunt, an artificial joint, an artificial hip joint, a blood bag, a blood reservoir, auxiliary instruments for operation, an adhesion preventing film, a wound covering material, etc. Here, the module for blood purification means a module having a function of removing wastes or a toxic substance in the blood by circulating the blood outside the body, and may be mentioned an artificial kidney, a toxin adhesion filter or column, etc.

Also, the coating film of the present invention is useful as a coating film of a cell culture vessel such as a flask, a dish, a plate, etc., or various kinds of equipments for research in which adhesion of a protein is suppressed.

Further, the coating film of the present invention is also useful as a material for cosmetics, a material for a contact lens care article, a fiber finishing agent for skin care, a material for a diagnostic agent for biochemical research, a blocking agent for suppressing non-specific adhesion in an enzyme-linked immunosorbent assay (ELISA) method or a latex aggregation method which has widely been used in the clinical diagnosis, a stabilizer for stabilizing a protein such as an enzyme and an antibody, etc.

Moreover, the coating film of the present invention is also useful as a coating film for toiletry, a personally care product, a detergent, a pharmaceutical product, a quasi-drug, fiber and an antifouling material.

The copolymer contained in the composition for forming a coating film and the sol according to the present invention particularly preferably used is a copolymer containing the recurring units of the following formula (a1) and the formula (b1).

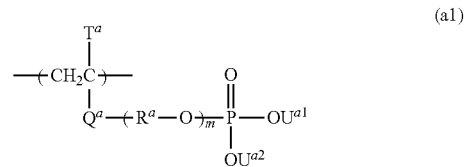

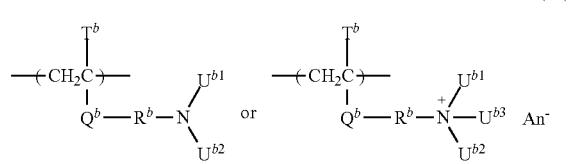

wherein $T^a$, $T^b$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom(s), An⁻ represents an anion selected from the group consisting of a halide ion, an inorganic acid ion, a hydroxide ion and an isothiocyanate ion, and m is an integer of 0 to 6.

In the present invention, "the ester bond" means —C(=O)—O— or —O—C(=O)—, and "the amide bond" means —NHC(=O)— or —C(=O)NH—.

In the present invention, "the linear or branched alkylene group having 1 to 10 carbon atom which may be substituted by a halogen atom(s)" means a linear or branched alkylene group having 1 to 10 carbon atoms or a linear or branched alkylene group having 1 to 10 carbon atoms substituted by one or more halogen atoms. Here, "the linear or branched alkylene group having 1 to 10 carbon atoms" is a divalent organic group corresponding to the above-mentioned alkyl group and may be mentioned, for example, a methylene group, an ethylene group, a propylene group, a trimethylene group, a tetramethylene group, a 1-methylpropylene group, a 2-methylpropylene group, a dimethylethylene group, an ethylethylene group, a pentamethylene group, a 1-methyltetramethylene group, a 2-methyl-tetramethylene group, a 1,1-dimethyl-trimethylene group, a 1,2-dimethyl-trimethylene group, a 2,2-dimethyl-trimethylene group, a 1-ethyl-trimethylene group, a hexamethylene group, an octamethylene group and a decamethylene group, etc., and among these, an ethylene group, a propylene group, an octamethylene group and a decamethylene group are preferred, a linear or branched alkylene group having 1 to 5 carbon atoms including, for example, an ethylene group, a propylene group, a trimethylene group and a tetramethylene group are more preferred, and an ethylene group or a propylene group is particularly preferred. "The linear or branched alkylene group having 1 to 10 carbon atoms substituted by one or more halogen atoms" means a group in which one or more optional hydrogen atoms of the above-mentioned alkylene group is/are substituted by a halogen atom(s), and particularly preferred is a group in which a part or whole of the hydrogen atoms of an ethylene group or a propylene group is/are substituted by a halogen atom(s).

The halogen atom may be mentioned a fluorine atom, a chlorine atom, a bromine atom and an iodine atom.

In the formula (a1), m is an integer of 0 to 6, preferably an integer of 0 to 3, more preferably an integer of 1 or 2, particularly preferably 1.

A ratio of the recurring unit of the formula (a1) contained in the copolymer according to the present invention is 20 mol % to 80 mol %, preferably 30 mol % to 70 mol %, more preferably 40 mol % to 60 mol %. Further, the copolymer according to the present invention may contain two or more kinds of the recurring units of the formula (a1).

A ratio of the recurring unit of the formula (b1) contained in the copolymer according to the present invention may be the whole remainder subtracting the ratio of the above-mentioned formula (a1) from the whole of the copolymer, or may be the remainder subtracting the total ratio of the above-mentioned formula (a1) and a third component mentioned below from the same. Further, the copolymer according to the present invention may contain two or more kinds of the recurring units of the formula (b1).

The copolymer contained in the composition for forming a coating film for forming the coating film of the present invention can be desirably synthesized by reacting (polymerizing) a monomer mixture containing the compounds of the following formula (A) and the formula (B):

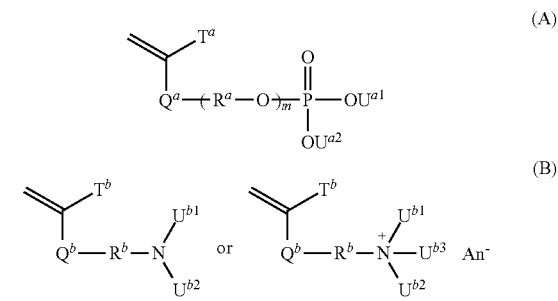

(wherein $T^a$, $T^b$, $U^{a1}$, $U^{a2}$, $U^{b1}$, $U^{b2}$ and $U^{b3}$ each independently represent a hydrogen atom or a linear or branched alkyl group having 1 to 5 carbon atoms, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom(s), An⁻ represents an anion selected from the group consisting of a halide ion, an inorganic acid ion, a hydroxide ion and an isothiocyanate ion, and m is an integer of 0 to 6) in a solvent.

Specific examples of the above-mentioned formula (A) include vinyl phosphonic acid, acid phosphoxy ethyl(meth)acrylate, 3-chloro-2-acid phosphoxypropyl(meth)acrylate, acid phosphoxypropyl(meth)acrylate, acid phosphoxymethyl(meth)acrylate, acid phosphoxypolyoxyethylene glycol mono(meth)acrylate, acid phosphoxypolyoxypropylene glycol mono(meth)acrylate, etc., and among these, vinyl phosphonic acid, acid phosphoxy ethyl methacrylate (=2-(methacryloyloxy)ethyl phosphate) and acid phosphoxypolyoxyethylene glycol monomethacrylate are preferably used.

The structural formulae of the vinyl phosphonic acid, acid phosphoxy ethyl methacrylate (=2-(methacryloyloxy)ethyl phosphate) and acid phosphoxypolyoxyethylene glycol monomethacrylate are shown by the following formula (A-1) to the formula (A-3), respectively.

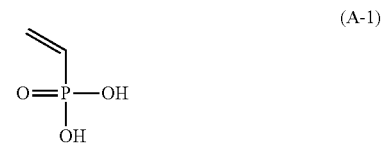

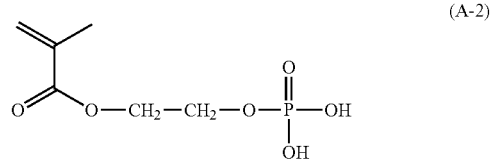

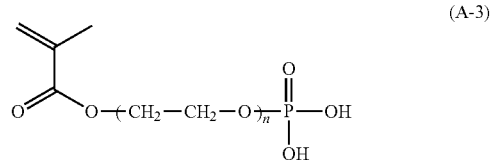

n = 4~5

These compounds may contain a (meth)acrylate compound having two functional groups of the formula (C) or (D) mentioned later at the time of synthesis in some cases.

Specific examples of the above-mentioned formula (B) include dimethylaminoethyl(meth)acrylate, diethylaminoethyl(meth)acrylate, dimethylaminopropyl(meth)acrylate, 2-(t-butylamino)ethyl(meth)acrylate, methacryloylcholine chloride, etc., and among these, dimethylaminoethyl(meth)acrylate, methacryloylcholine chloride or 2-(t-butylamino)ethyl(meth)acrylate is preferably used.

Structural formulae of the dimethylaminoethyl acrylate (=acrylic acid 2-(dimethylamino)ethyl), dimethylaminoethyl methacrylate (=2-(dimethylamino)ethyl methacrylate), methacryloylcholine chloride and 2-(t-butylamino)ethyl methacrylate (=methacrylic acid 2-(t-butylamino)ethyl are shown by the following formula (B-1) to the formula (B-4), respectively.

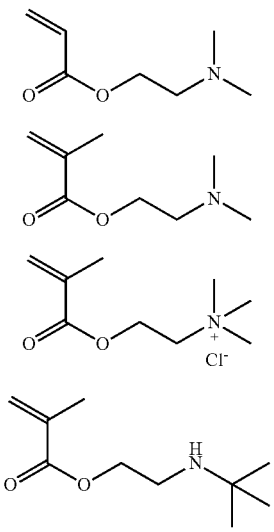

(B-1)
(B-2)
(B-3)
(B-4)

The copolymer according to the present invention may be further copolymerized with an optional third component. For example, as the third component, a (meth)acrylate compound having two or more functional groups may be copolymerized, and a part of the polymer may be partially three-dimensionally crosslinked. Such a third component may be mentioned, for example, a bifunctional monomer of the following formula (C) or (D):

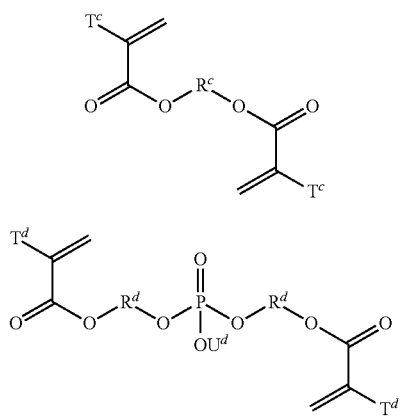

(C)
(D)

(wherein $T^c$, $T^d$ and $U^d$ each independently represent a hydrogen atom or a linear or branched alkyl group having 1 to 5 carbon atoms, $R^c$ and $R^d$ each independently represent a linear or branched alkylene group having 1 to 10 carbon atoms which may be substituted by a halogen atom(s)). That is, the copolymer according to the present invention may preferably contain a crosslinked structure derived from such a bifunctional monomer.

In the formulae (C) and (D), $T^c$ and $T^d$ are preferably each independently a hydrogen atom, a methyl group or an ethyl group, and more preferably each independently a hydrogen atom or a methyl group.

In the formulae (C) and (D), $U^d$ is preferably a hydrogen atom, a methyl group or an ethyl group, more preferably a hydrogen atom.

In the formulae (C) and (D), $R^c$ and $R^d$ each preferably independently represent a linear or branched alkylene group having 1 to 3 carbon atoms which may be substituted by a halogen atom(s), more preferably each independently represent an ethylene group or a propylene group, or an ethylene group or a propylene group substituted by one chlorine atom, particularly preferably an ethylene group or a propylene group.

The bifunctional monomer of the formula (C) may be preferably mentioned ethylene glycol di(meth)acrylate, triethylene glycol di(meth)acrylate, propylene glycol di(meth)acrylate, etc. The bifunctional monomer of the formula (D) may be preferably mentioned bis[(2-methacryloyloxy)methyl]phosphate, bis[(2-methacryloyloxy)ethyl]phosphate, bis[(2-methacryloyloxy)propyl]phosphate, etc.

In addition, as the trifunctional (meth)acrylate compound, phosphynylidine tris(oxy-2,1-ethane diyl)triacrylate may be mentioned.

Among these third component, ethylene glycol di(meth)acrylate and bis[2-(methacryloyloxy)ethyl]phosphate are particularly preferred, and their structural formulae are shown by the following formula (C-1) and the formula (D-1), respectively.

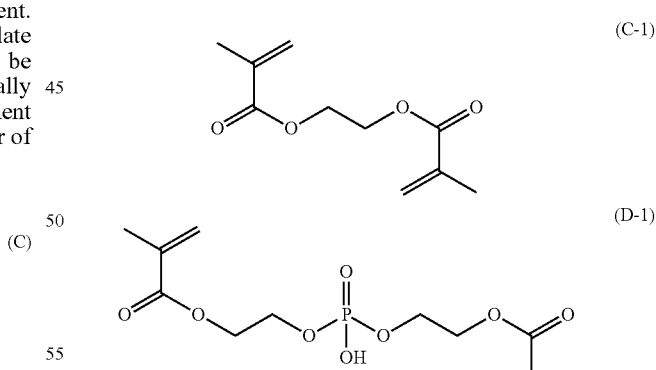

(C-1)
(D-1)

One or two or more kinds of these third components may be contained in the copolymer. Among the above-mentioned compounds, the bifunctional monomer of the formula (D) is preferred, and the bifunctional monomer of the formula (D-1) is particularly preferred.

A ratio of the third component in the above-mentioned copolymer, for example, cross-linked structure derived from the bifunctional monomer of the above-mentioned formula (C) or (D) is 0 mol % to 50 mol %.

A ratio of the compound of the formula (A) based on the whole monomers forming the above-mentioned copolymer is 20 mol % to 80 mol %, preferably 30 mol % to 70 mol %, more preferably 40 mol % to 60 mol %. In addition, the compound of the formula (A) may be two or more kinds.

A ratio of the compound of the formula (B) based on the whole monomers forming the above-mentioned copolymer may be the whole remainder subtracting the ratio of the above-mentioned formula (A) from the whole of the copolymer, or may be the remainder subtracting the total ratio of the above-mentioned formula (A) and the above-mentioned third component from the same. In addition, the compound of the formula (B) may be two or more kinds.

As the synthetic method of the copolymer according to the present invention, there may be mentioned the methods of radical polymerization, the anion polymerization, the cation polymerization, etc., which are general synthetic method of an acrylic polymer or a methacrylic polymer, etc., and a copolymer can be synthesized. As the reaction form thereof, various methods such as solution polymerization, suspension polymerization, emulsion polymerization, bulk polymerization, etc., may be employed.

The composition for forming a coating film according to the present invention may be prepared by diluting a desired the copolymer with a desired solvent and a desired concentration.

Further, the composition for forming a coating film according to the present invention may be prepared from the varnish containing the copolymer of the present invention. As one of the embodiments, the varnish containing the copolymer of the present invention can be prepared by the manufacturing method containing a process of reacting (polymerizing) the compounds of the above-mentioned formulae (A) and (B) in a solvent with a total concentration of the both compounds of 0.01% by mass to 4% by mass.

As the solvent in the polymerization reaction, it may be water, a phosphate buffered solution or an alcohol such as ethanol, etc., or a mixed solution in which these solvents are used in combination, and desirably contains water or ethanol. Further, it is preferred to contain water or ethanol in an amount of 10% by mass or more and 100% by mass or less. Moreover, it is preferred to contain water or ethanol in an amount of 50% by mass or more and 100% by mass or less. Furthermore, it is preferred to contain water or ethanol in an amount of 80% by mass or more and 100% by mass or less. Still further, it is preferred to contain water or ethanol in an amount of 90% by mass or more and 100% by mass or less. A total amount of water and ethanol is preferably 100% by mass.

As the reaction concentration, for example, it is preferred to make the concentration of the compounds of the above-mentioned formula (A) or the formula (B) in the reaction solvent 0.01% by mass to 4% by mass. If the concentration is 4% by mass or more, for example, there is sometimes a case that the copolymer is gelled in the reaction solvent due to strong associative property possessed by the phosphate group of the formula (A). If the concentration is 0.01% by mass or less, the concentration of the obtained varnish is too low, it is difficult to prepare the composition for forming a coating film for obtaining a coating film having a sufficient film thickness. The concentration is more preferably 0.01% by mass to 3% by mass, for example, 3% by mass or 2% by mass.

Also, in the synthesis of the copolymer according to the present invention, for example, after preparing an acidic phosphoric acid ester monomer (half salt) described in the formula (1), it may be polymerized to prepare the copolymer.

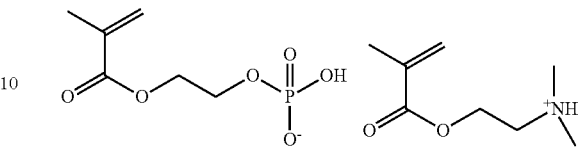

(1)

The phosphate group-containing monomer is a monomer easily associated, so that it may be added dropwise to the reaction solvent little by little so as to rapidly disperse therein when it is added dropwise to the reaction system.

Moreover, the reaction solvent may be heated (for example, 40° C. to 100° C.) to increase the solubility of the monomer and the polymer.

To proceed with polymerization reaction efficiently, a polymerization initiator is desirably used. Examples of the polymerization initiator to be used include 2,2'-azobis (isobutyronitrile), 2,2'-azobis(2-methylbutyronitrile), 2,2'-azobis(2,4-dimethylvaleronitrile), 4,4'-azobis(4-cyanovaleric acid), 2,2'-azobis(2,4-dimethylvaleronitrile), 2,2'-azobis (4-methoxy-2,4-dimethylvaleronitrile), 2,2'-azobis (isobutyronitrile), 1,1'-azobis(cyclohexan-1-carbonitrile), 1-[(1-cyano-1-methylethyl)azo]formamide, 2,2'-azobis[2-(2-imidazolin-2-yl)propane]dihydrochloride, 2,2'-azobis[2-(2-imidazolin-2-yl)propane], 2,2'-azobis(2-methylpropionamidine)dihydrochloride, 2,2'-azo(2-methyl-N-(2-hydroxyethyl)propionamide (Wako Pure Chemical Industries, Ltd., product name; VA-086, 10-hr half-life temperature; 86° C.), benzoyl peroxide (BPO), 2,2'-azobis(N-(2-carboxyethyl)-2-methylpropionamidine) n-hydrate (Wako Pure Chemical Industries, Ltd., product name; VA-057, 10-hr half-life temperature; 57° C.), 4,4'-azobis(4-cyanopentanoic acid) (Wako Pure Chemical Industries, Ltd., product name; VA-501), 2,2'-azobis[2-(2-imidazolidin-2-yl) propane]dihydrochloride (Wako Pure Chemical Industries, Ltd., product name; VA-044, 10-hr half-life temperature; 44° C.), 2,2'-azobis[2-(2-imidazolidin-2-yl)propane]disulfate dihydrate (Wako Pure Chemical Industries, Ltd., product name; VA-046B, 10-hr half-life temperature; 46° C.), 2,2'-azobis[2-(2-imidazolidin-2-yl)propane] (Wako Pure Chemical Industries, Ltd., product name; VA-061, 10-hr half-life temperature; 61° C.), 2,2'-azobis(2-amidinopropane)dihydrochloride (Wako Pure Chemical Industries, Ltd., product name; V-50, 10-hr half-life temperature; 56° C.), peroxodisulfate or t-butyl hydroperoxide, etc., and among these, taking ion balance and solubility in water into consideration, it is desired to use any of 2,2'-azobis[2-methyl-N-(2-hydroxyethyl)propionamide], 2,2'-azobis[N-(2-carboxyethyl)-2-methylpropionamidine] n-hydrate, 4,4'-azobis(4-cyanopentanoic acid), 2,2'-azobis[2-(2-imidazolidin-2-yl) propane]dihydrochloride, 2,2'-azobis[2-(2-imidazolidin-2-yl)propane]disulfate dihydrate, 2,2'-azobis[2-(2-imidazolidin-2-yl)propane], 2,2'-azobis(2-amidinopropane) dihydrochloride and peroxodisulfate.

An amount of the polymerization initiator to be added is 0.05% by mass to 10% by mass based on the total weight of the monomer to be used for the polymerization.

As the reaction conditions, the polymerization reaction proceeds by heating a reaction vessel by an oil bath, etc., at 50° C. to 200° C. and stirring for 1 hour to 48 hours, more preferably at 80° C. to 150° C. for 5 hours to 30 hours to obtain the copolymer of the present invention. The reaction atmosphere is preferably a nitrogen atmosphere.

As the reaction procedure, the whole reaction substances are charged in the reaction solvent at the room temperature, and then, the polymerization may be carried out by heating to the above-mentioned temperature, or whole or a part of the mixture of the reaction substances may be added dropwise to the previously heated solvent little by little.

According to the latter reaction procedure, the varnish containing the copolymer of the present invention can be prepared by the manufacturing method comprising a process of adding a mixture containing the compounds of the above-mentioned formulae (A) and (B), a solvent and a polymerization initiator dropwise to the solvent maintained at a temperature higher than the 10-hr half-life temperature of the polymerization initiator, and reacting (polymerizing) the compounds.

According to this embodiment, by employing the above-mentioned reaction procedure and the temperature conditions, a concentration of the compounds of the above-mentioned formulae (A) and (B) in the reaction solvent can be made, for example, 0.01% by mass to 10% by mass. In this embodiment, even if the concentration exceeds 4% by mass, the dropping phase and the reaction phase become a transparent uniform solution before the reaction, and gelation of the copolymer in the reaction solvent after the reaction can be suppressed. Other conditions in this embodiment are the same as mentioned above.

A molecular weight of the copolymer according to the present invention may be several thousand to several million or so, preferably 5,000 to 5,000,000. It is more preferably 10,000 to 2,000,000. Also, it may be either of a random copolymer, a block copolymer or a graft copolymer, there is no specific limitation in the copolymerization reaction itself for manufacturing the copolymer, and a conventionally known method synthesized in a solution such as radical polymerization, ion polymerization, or polymerization utilizing photopolymerization, macromer or emulsion polymerization can be used. Depending on the purposes thereof to be used, any one of the copolymers of the present invention may be solely used, or plural kinds of the copolymers may be used by mixing with appropriately changing the ratios thereof.

Also, the various copolymers manufactured as mentioned above may be a two-dimensional polymer or a three-dimensional polymer, and is in a state of dispersing in a solution containing water. That is, in the varnish containing these polymers, it is not preferred to cause ununiform gelation or turbid precipitation, and a transparent varnish, a dispersed colloidal varnish or a sol is preferred.

The copolymer according to the present invention has both of the cation and the anion in the molecule, so that it becomes a sol by bonding the copolymers to each other due to ionic bonding in some cases. Also, as mentioned above, for example, in the case of a copolymer in which a (meth) acrylate compound(s) having two or more functional groups is/are copolymerized as a third component, a part of the copolymer is partially three-dimensionally crosslinked to form a sol in some cases.

The sol of the present invention has an average particle diameter of 2 nm or more and 500 nm or less in particle diameter distribution measured by the dynamic light scattering method. More preferred average particle diameter is 2 nm or more and 400 nm or less, further preferred average particle diameter is 2 nm or more and 300 nm or less, and the most preferred average particle diameter is 2 nm or more and 200 nm or less.

Further, the present invention relates to use of the composition for forming a coating film which comprises the copolymer containing the above-mentioned recurring unit containing an organic group of the formula (a) and the above-mentioned recurring unit containing an organic group of the formula (b), and a solvent, in the coating of a substrate. Moreover, the present invention also relates to use of the composition for forming a coating film which comprises the copolymer containing the above-mentioned recurring unit containing an organic group of the formula (a) and the above-mentioned recurring unit containing an organic group of the formula (b), and a solvent, for suppressing adhesion of a biological substance. Specific examples of the copolymer, the solvent and the substrate, etc., and specific embodiments of use of the composition are as mentioned above.

EXAMPLES

In the following, the present invention is explained further in detail by referring to Synthetic examples and Examples, but the present invention is not limited by these.

A weight average molecular weight shown in the following Synthetic example is a measurement result by Gel Filtration Chromatography (in the following, it is abbreviated to as GFC). The measurement conditions, etc., are as follows.

Device: Prominence (manufactured by Shimadzu Corporation)
GFC column: TSKgel GMPWXL (7.8 mm I.D.×30 cm)×2
Flow rate: 1.0 ml/min
Eluent: ionic aqueous solution
Column temperature: 40° C.
Detector: RI
Injection concentration: Polymer solid content 0.1% by mass
Injection amount: 100 uL
Calibration curve: Cubic approximate curve
Standard sample: Polyethylene oxide (available from Agilent Technologies Japan, Ltd.)×10 kinds <Measurement Method of Raw Material Composition>

Measurement of a concentration (% by mass) of each phosphorous-containing compound which is a raw material containing a phosphorus-containing compound was carried out by $^{31}$P-NMR. An absolute concentration (absolute % by mass) of each phosphorus-containing compound contained in the raw materials was calculated by using the following standard substance.

(Measurement Conditions)
Mode: reverse gate decoupling mode (quantitative mode)
Device: Varian 400 MHz
Solvent: $CD_3OD$ (deuterated methanol) (30% by weight)
Rotation number: 0 Hz
Data point: 64,000
Flip angle: 90°
Waiting time: 70 s
Integration times: 16 times, n=4,
Standard substance: trimethylphosphate+$D_2O$ (75% TMP solution was prepared)

Synthetic Example 1

6.00 g of acid phosphoxy ethyl methacrylate (the compound of the formula (A-2), Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)), 4.12 g of 2-(dimethylamino)ethyl methacrylate (the compound of the formula (B-2), available from Tokyo Chemical Industry Co., Ltd.) and 0.24 g of 2,2'-azo(2-methyl-N-(2-hydroxyethyl) propionamide) (Product name; VA-086, available from Wako Pure Chemical Industries, Ltd.) were dissolved in 446.34 g of pure water and 49.59 g of ethanol, and charged in a recovery flask, and subjected to nitrogen purge by blowing nitrogen thereinto, and then subjected to polymerization reaction in an oil bath at 100° C. for 24 hours to obtain 506.05 g of a varnish containing a copolymer with a solid content of 2% by mass.

Synthetic Example 2

6.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyl-oxy)ethyl]phosphate (28.6% by mass) and other substances (27.2% by mass)), 4.12 g of 2-(dimethylamino)ethyl methacrylate (available from Tokyo Chemical Industry Co., Ltd.) and 0.24 g of 2,2'-azo(2-methyl-N-(2-hydroxyethyl)propionamide) (Product name; VA-086, available from Wako Pure Chemical Industries, Ltd.) were dissolved in 490.87 g of pure water, and charged in a recovery flask, and subjected to nitrogen purge by blowing nitrogen thereinto, and then subjected to polymerization reaction in an oil bath at 100° C. for 24 hours to obtain 506.05 g of a varnish containing a copolymer with a solid content of 3% by mass.

Synthetic Example 3

6.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy) ethyl]phosphate (28.6% by mass) and other substances (27.2% by mass)), 4.12 g of 2-(dimethylamino)ethyl methacrylate (available from Tokyo Chemical Industry Co., Ltd.) and 0.24 g of 2,2'-azo(2-methyl-N-(2-hydroxyethyl)propionamide) (Product name; VA-086, available from Wako Pure Chemical Industries, Ltd.) were dissolved in 490.87 g of PBS (phosphate buffered physiological saline, available from Sigma-Aldrich Co. LLC.), and charged in a recovery flask, and subjected to nitrogen purge by blowing nitrogen thereinto, and then subjected to polymerization reaction in an oil bath at 100° C. for 24 hours to obtain 506.05 g of a varnish containing a copolymer with a solid content of 3% by mass.

Synthetic Example 4

0.3 g of pure water was added to 1.50 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)), into the mixture while stirring at 60° C. was added dropwise 1.03 g of 2-(dimethylamino)ethyl methacrylate (available from Tokyo Chemical Industry Co., Ltd.) over 3 hours, and the resulting mixture was then stirred at 70° C. for 12 hours to prepare a half salt hydrate. The above-mentioned half salt hydrate was heated to 60° C. by an evaporator to evaporate water, and a material a water content of which became 1% or less was made 2-(dimethylamino)ethyl methacrylate half salt (the compound of the formula (1)) of the acid phosphoxy ethyl methacrylate. To the half salt was added 0.03 g of 2,2'-azo (2-methyl-N-(2-hydroxyethyl)propionamide (Product name; VA-086, available from Wako Pure Chemical Industries, Ltd.), and dissolved in 73.63 g of pure water and 8.18 g of ethanol, the mixture was charged in a recovery flask, and subjected to nitrogen purge by blowing nitrogen thereinto, and then subjected to polymerization reaction in an oil bath at 100° C. for 24 hours to obtain 84.34 g of a varnish containing a copolymer with a solid content of 3% by mass.

Synthetic Example 5

12.40 g of pure water was added to 6.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and sufficiently dissolved, then, 12.40 g of ethanol, 4.12 g of 2-(dimethylamino)ethyl methacrylate (available from Tokyo Chemical Industry Co., Ltd.) and 0.10 g of 2,2'-azo(2-methyl-N-(2-hydroxyethyl)propionamide) (Product name; VA-086, available from Wako Pure Chemical Industries, Ltd.) were further successively added to the aqueous solution of Phosmer M while maintaining at 20° C. or lower. The mixed solution into which the above-mentioned all materials have been entered which had been sufficiently stirred to become uniform was introduced into a dropping funnel. On the other hand, 471.13 g of pure water and 37.20 g of ethanol were separately charged into a three-necked flask equipped with a condenser, this was subjected to nitrogen flow, and raised to a reflux temperature while stirring. While maintaining the state, the dropping funnel into which the above-mentioned mixed solution had been introduced was set to the three-necked flask, and the mixed solution was added dropwise into a boiled solution of pure water and ethanol over 0.5 hour. After dropping, the mixture was stirred under heating while maintaining the above-mentioned circumstance for 24 hours to obtain 506.05 g of a transparent polymer solution with a solid content of about 2% by mass. A weight average molecular weight of the obtained transparent liquid by GFC was about 810,000.

Synthetic Example 6

68.88 g of pure water was added to 10.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and sufficiently dissolved, then, 29.52 g of ethanol, 7.63 g of 2-(dimethylamino)ethyl methacrylate (available from Tokyo Chemical Industry Co., Ltd.) and 0.09 g of 2,2'-azobis[N-(2-carboxyethyl)-2-methylpropionamidine] (Product name; VA-057, available from Wako Pure Chemical Industries, Ltd.) were further successively added to the aqueous solution of Phosmer M while maintaining at 20° C. or lower. The mixed solution into which the above-mentioned all materials have been entered which had been sufficiently stirred to become uniform was introduced into a dropping funnel. On the other hand, 373.89 g of pure water and 29.52 g of ethanol were separately charged into a three-necked flask equipped with a condenser, this was subjected to nitrogen flow, and raised to a reflux temperature while stirring. While maintaining the state, the dropping funnel into which the above-mentioned mixed solution had been introduced was set to the three-necked flask, and the mixed solution was added dropwise into a boiled solution of pure water and ethanol over 0.5 hour. After dropping, the mixture was stirred under heating while maintaining the above-mentioned circumstance for 24 hours to obtain 509.60 g of a transparent polymer solution with a solid content of about 3.5% by mass. A weight average molecular weight of the obtained transparent liquid by GFC was about 280,000.

Synthetic Example 7

56.56 g of pure water was added to 12.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and sufficiently dissolved, then, 24.24 g of ethanol, 9.16 g of 2-(dimethylamino)ethyl methacrylate (available from Tokyo Chemical Industry Co., Ltd.) and 0.11 g of 2,2'-azobis[N-(2-carboxyethyl)-2-methylpropionamidine] (Product name; VA-057, available from Wako Pure Chemical Industries, Ltd.) were further successively added to the aqueous solution of Phosmer M while maintaining at 20° C. or lower. The mixed solution into which the above-mentioned all materials have been entered which had been sufficiently stirred to become uniform was introduced into a dropping funnel. On the other hand, 307.05 g of pure water and 16.16 g of ethanol were separately charged into a three-necked flask equipped with a condenser, this was subjected to nitrogen flow, and raised to a reflux temperature while stirring. While maintaining the state, the dropping funnel into which the above-mentioned mixed solution had been introduced was set to the three-necked flask, and the mixed solution was added dropwise into a boiled solution of pure water and ethanol over 0.5 hour. After dropping, the mixture was stirred under heating while maintaining the above-mentioned circumstance for 24 hours to obtain 425.28 g of a transparent polymer solution with a solid content of about 5% by mass. A weight average molecular weight of the obtained transparent liquid by GFC was about 610,000.

Synthetic Example 8

54.41 g of pure water was added to 14.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and sufficiently dissolved, then, 23.32 g of ethanol, 10.68 g of 2-(dimethylamino)ethyl methacrylate (available from Tokyo Chemical Industry Co., Ltd.) and 0.12 g of 2,2'-azobis[N-(2-carboxyethyl)-2-methylpropionamidine] (Product name; VA-057, available from Wako Pure Chemical Industries, Ltd.) were further successively added to the aqueous solution of Phosmer M while maintaining at 20° C. or lower. The mixed solution into which the above-mentioned all materials have been entered which had been sufficiently stirred to become uniform was introduced into a dropping funnel. On the other hand, 295.38 g of pure water and 15.55 g of ethanol were separately charged into a three-necked flask equipped with a condenser, this was subjected to nitrogen flow, and raised to a reflux temperature while stirring. While maintaining the state, the dropping funnel into which the above-mentioned mixed solution had been introduced was set to the three-necked flask, and the mixed solution was added dropwise into a boiled solution of pure water and ethanol over 0.5 hour. After dropping, the mixture was stirred under heating while maintaining the above-mentioned circumstance for 24 hours to obtain 413.47 g of a transparent polymer solution with a solid content of about 6% by mass. A weight average molecular weight of the obtained transparent liquid by GFC was about 1,010,000.

Synthetic Example 9

7.63 g of 2-(dimethylamino)ethyl methacrylate (available from Tokyo Chemical Industry Co., Ltd.) was added to 10.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy) ethyl]phosphate (28.6% by mass) and other substances (27.2% by mass)), and the mixture was stirred at room temperature until it became 30° C. or lower for about 1 hour. Then, 59.24 g of pure water, 25.39 g of ethanol and 0.09 g of 2,2'-azobis[N-(2-carboxyethyl)-2-methylpropionamidine] (Product name; VA-057, available from Wako Pure Chemical Industries, Ltd.) were further successively added to the aqueous solution of Phosmer M while maintaining at 20° C. or lower. The mixed solution into which the above-mentioned all materials have been entered which had been sufficiently stirred to become uniform was introduced into a dropping funnel. On the other hand, 321.61 g of pure water and 16.93 g of ethanol were separately charged into a three-necked flask equipped with a condenser, this was subjected to nitrogen flow, and raised to a reflux temperature while stirring. While maintaining the state, the dropping funnel into which the above-mentioned mixed solution had been introduced was set to the three-necked flask, and the mixed solution was added dropwise into a boiled solution of pure water and ethanol over 0.5 hour. After dropping, the mixture was stirred under heating while maintaining the above-mentioned circumstance for 24 hours to obtain 440.80 g of a transparent polymer solution with a solid content of about 4% by mass. A weight average molecular weight of the obtained transparent liquid by GFC was about 500,000.

Synthetic Example 10

51.32 g of pure water was added to 2.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and sufficiently dissolved, then, 21.99 g of ethanol, 1.53 g of 2-(dimethylamino)ethyl methacrylate (available from Tokyo Chemical Industry Co., Ltd.) and 0.18 g of 2,2'-azobis[N-(2-carboxyethyl)-2-methylpropionamidine] (Product name; VA-057, available from Wako Pure Chemical Industries, Ltd.) were further successively added to the aqueous solution of Phosmer M while maintaining at 20° C. or lower. The mixed solution into which the above-mentioned all materials have been entered which had been sufficiently stirred to become uniform was introduced into a dropping funnel. On the other hand, 278.59 g of pure water and 14.66 g of ethanol were separately charged into a three-necked flask equipped with a condenser, this was subjected to nitrogen flow, and raised to a reflux temperature while stirring. While maintaining the state, the dropping funnel into which the above-mentioned mixed solution had been introduced was set to the three-necked flask, and the mixed solution was added dropwise into a boiled solution of pure water and ethanol over 0.5 hour. After dropping, the mixture was stirred under heating while maintaining the above-mentioned circumstance for 24 hours to obtain 370.10 g of a transparent polymer solution with a solid content of about 1% by mass. A weight average molecular weight of the obtained transparent liquid by GFC was about 38,000.

Synthetic Example 11

50.93 g of pure water was added to 6.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and sufficiently dissolved, then, 21.83 g of ethanol, 9.16 g of 2-(dimethylamino)ethyl methacrylate (available from Tokyo Chemical Industry Co., Ltd.) and 0.08 g of 2,2'-azobis[N-(2-carboxyethyl)-2-methylpropionamidine] (Product name; VA-057, available from Wako Pure Chemical Industries, Ltd.) were further successively added to the aqueous solution of Phosmer M while maintaining at 20° C. or lower. The mixed solution into which the above-mentioned all materials have been entered which had been sufficiently stirred to become uniform was introduced into a dropping funnel. On the other hand, 276.49 g of pure water and 14.55 g of ethanol were separately charged into a three-necked flask equipped with a condenser, this was subjected to nitrogen flow, and raised to a reflux temperature while stirring. While maintaining the state, the dropping funnel into which the above-mentioned mixed solution had been introduced was set to the three-necked flask, and the mixed solution was added dropwise into a boiled solution of pure water and ethanol over 0.5 hour. After dropping, the mixture was stirred under heating while maintaining the above-mentioned circumstance for 24 hours to obtain 378.96 g of a transparent polymer solution with a solid content of about 4% by mass. A weight average molecular weight of the obtained transparent liquid by GFC was about 720,000.

Synthetic Example 12

64.03 g of pure water was added to 10.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and sufficiently dissolved, then, 27.44 g of ethanol, 8.96 g of 2-(di-ethylamino)ethyl methacrylate (available from Tokyo Chemical Industry Co., Ltd.) and 0.09 g of 2,2'-azobis[N-(2-carboxyethyl)-2-methylpropionamidine] (Product name; VA-057, available from Wako Pure Chemical Industries, Ltd.) were further successively added to the aqueous solution of Phosmer M while maintaining at 20° C. or lower. The mixed solution into which the above-mentioned all materials have been entered which had been sufficiently stirred to become uniform was introduced into a dropping funnel. On the other hand, 347.60 g of pure water and 18.29 g of ethanol were separately charged into a three-necked flask equipped with a condenser, this was subjected to nitrogen flow, and raised to a reflux temperature while stirring. While maintaining the state, the dropping funnel into which the above-mentioned mixed solution had been introduced was set to the three-necked flask, and the mixed solution was added dropwise into a boiled solution of pure water and ethanol over 0.5 hour. After dropping, the mixture was stirred under heating while maintaining the above-mentioned circumstance for 24 hours to obtain 476.33 g of a transparent polymer solution with a solid content of about 4% by mass. A weight average molecular weight of the obtained transparent liquid by GFC was about 290,000.

Synthetic Example 13

56.58 g of pure water was added to 7.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and sufficiently dissolved, then, 47.15 g of ethanol, 12.55 g of 2-(diethylamino)ethyl methacrylate (available from Tokyo Chemical Industry Co., Ltd.) and 0.10 g of 2,2'-azobis[N-(2-carboxyethyl)-2-methylpropionamidine] (Product name; VA-057, available from Wako Pure Chemical Industries, Ltd.) were further successively added to the aqueous solution of Phosmer M while maintaining at 20° C. or lower. The mixed solution into which the above-mentioned all materials have been entered which had been sufficiently stirred to become uniform was introduced into a dropping funnel. On the other hand, 367.75 g of pure water was separately charged into a three-necked flask equipped with a condenser, this was subjected to nitrogen flow, and raised to a reflux temperature while stirring. While maintaining the state, the dropping funnel into which the above-mentioned mixed solution had been introduced was set to the three-necked flask, and the mixed solution was added dropwise into a boiled solution of pure water and ethanol over 0.5 hour. After dropping, the mixture was stirred under heating while maintaining the above-mentioned circumstance for 24 hours to obtain 491.02 g of a slightly turbid polymer solution with a solid content of about 4% by mass. A weight average molecular weight of the obtained liquid by GFC after filtration was about 300,000.

Synthetic Example 14

60.64 g of pure water was added to 9.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and sufficiently dissolved, then, 17.33 g of ethanol, 11.31 g of 80% methacryloylcholine chloride aqueous solution (available from Tokyo Chemical Industry Co., Ltd.) and 0.10 g of 2,2'-azobis[N-(2-carboxyethyl)-2-methylpropionamidine] (Product name; VA-057, available from Wako Pure Chemical Industries, Ltd.) were further successively added to the aqueous solution of Phosmer M while maintaining at 20° C. or lower. The mixed solution into which the above-mentioned all materials have been entered which had been sufficiently stirred to become uniform was introduced into a dropping funnel. On the other hand, 326.94 g of pure water and 17.33 g of ethanol were separately charged into a three-necked flask equipped with a condenser, this was subjected to nitrogen flow, and raised to a reflux temperature while stirring. While maintaining the state, the dropping funnel into which the mixed solution had been introduced was set to the three-necked flask, and the mixed solution was added dropwise into a boiled solution of pure water and ethanol over 0.5 hour. After dropping, the mixture was stirred under heating while maintaining the above-mentioned circumstance for 24 hours to obtain 453.48 g of a transparent polymer solution with a solid content of about 4% by mass. A weight average molecular weight of the obtained transparent liquid by GFC was about 130,000.

Synthetic Example 15

56.95 g of pure water was added to 10.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and sufficiently dissolved, then, 24.41 g of ethanol, 6.95 g of 2-(dimethylamino)ethyl acrylate (the compound of the formula (B-1), available from Tokyo Chemical Industry Co., Ltd.) and 0.0848 g of 2,2'-azobis[N-(2-carboxyethyl)-2-methylpropionamidine] (Product name; VA-057, available from Wako Pure Chemical Industries, Ltd.) were further successively added to the aqueous solution of Phosmer M while maintaining at 20° C. or lower. The mixed solution into which the above-mentioned all materials have been entered which had been sufficiently stirred to become uniform was introduced into a dropping funnel. On the other hand, 56.95 g of pure water and 16.27 g of ethanol were separately charged into a three-necked flask equipped with a condenser, this was subjected to nitrogen flow, and raised to a reflux temperature while stirring. While maintaining the state, the dropping funnel into which the above-mentioned mixed solution had been introduced was set, and the mixed solution was added dropwise into a boiled solution of pure water and ethanol over 0.5 hour. After dropping, the mixture was stirred under heating while maintaining the above-mentioned circumstance for 24 hours to obtain 423.77 g of a transparent polymer solution with a solid content of about 4% by mass. A weight average molecular weight of the obtained transparent liquid by GFC was about 150,000.

Synthetic Example 16

59.89 g of pure water was added to 10.00 g of acid phosphoxy ethyl methacrylate (Product name; LIGHT ESTER P-1M, available from Kyoeisha Chemical Co., Ltd., a mixture of acid phosphoxy ethyl methacrylate (42.2% by mass), bis[2-(methacryloyloxy)ethyl]phosphate (16.9% by mass) and other substances (40.9% by mass)) and sufficiently dissolved, then, 25.67 g of ethanol, 7.83 g of 2-(dimethylamino)ethyl methacrylate (available from Tokyo Chemical Industry Co., Ltd.) and 0.09 g of 2,2'-azobis[N-(2-carboxyethyl)-2-methylpropionamidine] (Product name; VA-057, available from Wako Pure Chemical Industries, Ltd.) were further successively added to the aqueous solution of LIGHT ESTER P-1M while maintaining at 20° C. or lower. The mixed solution into which the above-mentioned all materials have been entered which had been sufficiently stirred to become uniform was introduced into a dropping funnel. On the other hand, 325.13 g of pure water and 17.11 g of ethanol were separately charged into a three-necked flask equipped with a condenser, this was subjected to nitrogen flow, and raised to a reflux temperature while stirring. While maintaining the state, the dropping funnel into which the above-mentioned mixed solution had been introduced was set to the three-necked flask, and the mixed solution was added dropwise into a boiled solution of pure water and ethanol over 0.5 hour. After dropping, the mixture was stirred under heating while maintaining the above-mentioned circumstance for 24 hours to obtain 445.63 g of a transparent polymer solution with a solid content of about 4% by mass. A weight average molecular weight of the obtained transparent liquid by GFC was about 410,000.

Synthetic Example 17

47.84 g of pure water was added to 10.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and sufficiently dissolved, then, 15.95 g of ethanol, 7.63 g of 2-(dimethylamino)ethyl methacrylate (available from Tokyo Chemical Industry Co., Ltd.) and 0.09 g of 2,2'-azobis[N-(2-carboxyethyl)-2-methylpropionamidine] (Product name; VA-057, available from Wako Pure Chemical Industries, Ltd.) were further successively added to the aqueous solution of Phosmer M while maintaining at 20° C. or lower. The mixed solution into which the above-mentioned all materials have been entered which had been sufficiently stirred to become uniform was introduced into a dropping funnel. On the other hand, 95.69 g of pure water was separately charged into a three-necked flask equipped with a condenser, this was subjected to nitrogen flow, and raised to a reflux temperature while stirring. While maintaining the state, the dropping funnel into which the above-mentioned mixed solution had been introduced was set to the three-necked flask, and the mixed solution was added dropwise into a boiled solution of pure water and ethanol over 1 hour. After dropping, the mixture was stirred under heating while maintaining the above-mentioned circumstance for 24 hours to obtain 177.11 g of a transparent polymer solution with a solid content of about 10% by mass. A weight average molecular weight of the obtained transparent liquid by GFC was about 582,000.

Synthetic Example 18

25.39 g of pure water was added to 5.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and sufficiently dissolved, then, 10.88 g of ethanol, 4.50 g of 2-((t-butylamino)ethyl methacrylate (available from Sigma-Aldrich Co. LLC.) and 0.05 g of 2,2'-azobis[N-(2-carboxyethyl)-2-methylpropionamidine] (Product name; VA-057, available from Wako Pure Chemical Industries, Ltd.) were further successively added to the aqueous solution of Phosmer M while maintaining at 20° C. or lower. The mixed solution into which the above-mentioned all materials have been entered which had been sufficiently stirred to become uniform was introduced into a dropping funnel. On the other hand, 137.82 g of pure water and 7.25 g of ethanol were separately charged into a three-necked flask equipped with a condenser, this was subjected to nitrogen flow, and raised to a reflux temperature while stirring. While maintaining the state, the dropping funnel into which the above-mentioned mixed solution had been introduced was set to the three-necked flask, and the mixed solution was added dropwise into a boiled solution of pure water and ethanol over 0.5 hour. After dropping, the mixture was stirred under heating while maintaining the above-mentioned circumstance for 24 hours to obtain 190.84 g of a transparent polymer solution with a solid content of about 5% by mass. A weight average molecular weight of the obtained transparent liquid by GFC was about 225,000.

Synthetic Example 19

19.54 g of pure water was added to 5.00 g of acid phosphoxypolyoxyethylene glycol monomethacrylate (Product name; Phosmer PE, available from Unichemical Co., Ltd., a non-volatile component by the dryness method at 100° C. for 1 hour: 94.9%) and sufficiently dissolved, then, 8.37 g of ethanol, 2.31 g of 2-(dimethylamino)ethyl methacrylate (available from Tokyo Chemical Industry Co., Ltd.) and 0.04 g of 2,2'-azobis[N-(2-carboxyethyl)-2-methylpropionamidine] (Product name; VA-057, available from Wako Pure Chemical Industries, Ltd.) were further successively added to the aqueous solution of Phosmer PE while maintaining at 20° C. or lower. The mixed solution into which the above-mentioned all materials have been entered which had been sufficiently stirred to become uniform was introduced into a dropping funnel. On the other hand, 106.05 g of pure water and 5.58 g of ethanol were separately charged into a three-necked flask equipped with a condenser, this was subjected to nitrogen flow, and raised to a reflux temperature while stirring. While maintaining the state, the dropping funnel into which the above-mentioned mixed solution had been introduced was set to the three-necked flask, and the mixed solution was added dropwise into a boiled solution of pure water and ethanol over 0.5 hour. After dropping, the mixture was stirred under heating while maintaining the above-mentioned circumstance for 24 hours to obtain 146.84 g of a transparent polymer solution with a solid content of about 5% by mass. A weight average molecular weight of the obtained transparent liquid by GFC was about 146,000.

Synthetic Example 20

To 43.73 g of pure water was added 0.12 g of 2,2'-azobis[N-(2-carboxyethyl)-2-methylpropionamidine] (Product name; VA-057, available from Wako Pure Chemical Industries, Ltd.) while maintaining at 20° C. or lower, and the VA-057 aqueous solution which has been uniform by sufficiently stirring was introduced into a dropping funnel. On the other hand, 174.92 g of pure water was separately added to 10.00 g of vinyl phosphonic acid (the compound of the formula (A-1), available from Tokyo Chemical Industry Co., Ltd.) and sufficiently dissolved, then, 14.17 g of 2-(dimethylamino)ethyl methacrylate (available from Tokyo Chemical Industry Co., Ltd.) was further added and dissolved therein by sufficiently stirring. The mixed solution was charged into a three-necked flask equipped with a condenser, subjected to nitrogen flow, and raised the temperature to 60° C. under stirring. While maintaining the state, the dropping funnel into which the above-mentioned VA-057 aqueous solution had been introduced was set, and the mixed solution was added dropwise into a boiled solution of pure water and ethanol over 0.5 hour. After dropping, the mixture was stirred under heating while maintaining the above-mentioned circumstance for 24 hours to obtain 242.83 g of a transparent polymer solution with a solid content of about 10% by mass. A weight average molecular weight of the obtained transparent liquid by GFC was about 535,000.

Comparative Synthetic Example 1

In 58.20 g of pure water and 6.47 g of ethanol were dissolved 2.00 g of 2-methacryloyloxyethyl phosphorylcholine (available from Tokyo Chemical Industry Co., Ltd.) and 0.02 g of 2,2'-azo(2-methyl-N-(2-hydroxyethyl)propionamide) (Product name; VA-086, available from Wako Pure Chemical Industries, Ltd.) were dissolved in 58.20 g of pure water and 6.47 g of ethanol, and charged in a recovery flask, and subjected to nitrogen purge by blowing nitrogen thereinto, and then subjected to polymerization reaction in an oil bath at 100° C. for 24 hours to obtain 506.05 g of a varnish containing a copolymer with a solid content of 3% by mass.

Comparative Synthetic Example 2

6.00 g of acid phosphoxy ethyl methacrylate (the compound of the formula (A-2), Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)), 4.12 g of 2-(dimethylamino)ethyl methacrylate (the compound of the formula (B-2), available from Tokyo Chemical Industry Co., Ltd.) and 0.24 g of 2,2'-azo(2-methyl-N-(2-hydroxyethyl) propionamide (Product name; VA-086, available from Wako Pure Chemical Industries, Ltd.) were dissolved in 173.07 g of pure water and 19.23 g of ethanol, and charged in a recovery flask, and subjected to nitrogen purge by blowing nitrogen thereinto, and then subjected to polymerization reaction in an oil bath at 100° C. for 24 hours to expect to obtain a varnish containing a copolymer with a solid content of 5% by mass, but the obtained material was a turbid gel-state solution a solid of which was attached to the edge of the flask.

Comparative Synthetic Example 3

0.3 g of pure water was added to 1.50 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)), into the mixture while stirring at 60° C., 1.03 g of 2-(dimethylamino)ethyl methacrylate (available from Tokyo Chemical Industry Co., Ltd.) was added dropwise over 3 hours, and the resulting mixture was thereafter stirred at 70° C. for 12 hours to prepare a half salt hydrate. The above-mentioned half salt hydrate was heated up to 60° C. by an evaporator to evaporate water, and a material a water content of which became 1% or less was made 2-(dimethylamino)ethyl methacrylate half salt (the compound of the formula (1)) of the acid phosphoxy ethyl methacrylate. To 2.53 g of the half salt was added 0.03 g of 2,2'-azo(2-methyl-N-(2-hydroxyethyl)propionamide) (Product name; VA-086, available from Wako Pure Chemical Industries, Ltd.), and dissolved in 43.27 g of pure water and 4.81 g of ethanol, the mixture was charged in a recovery flask, and subjected to nitrogen purge by blowing nitrogen thereinto, and then subjected to polymerization reaction in an oil bath at 100° C. for 24 hours to expect to obtain a varnish containing a copolymer with a solid content of 5% by mass, but the obtained material was a turbid gel-state solution a solid of which was attached to the edge of the flask.

Comparative Synthetic Example 4

38.98 g of pure water was added to 10.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and sufficiently dissolved, then, 12.99 g of ethanol, 7.63 g of 2-(dimethylamino)ethyl methacrylate (available from Tokyo Chemical Industry Co., Ltd.) and 0.09 g of 2,2'-azobis[N-(2-carboxyethyl)-2-methylpropionamidine] (Product name; VA-057, available from Wako Pure Chemical Industries, Ltd.) were further successively added to the aqueous solution of Phosmer M while maintaining at 20° C. or lower. The mixed solution into which the above-mentioned all materials have been entered which had been sufficiently stirred to become uniform was introduced into a dropping funnel. On the other hand, 77.97 g of pure water was separately charged into a three-necked flask equipped with a condenser, this was subjected to nitrogen flow, and raised to a reflux temperature while stirring. While maintaining the state, the dropping funnel into which the above-mentioned mixed solution had been introduced was set to the three-necked flask, and the mixed solution was added dropwise into a boiled solution of pure water and ethanol over 1 hour. After dropping, the mixture was stirred under heating while maintaining the above-mentioned circumstance, then, it became a gelled solid within 10 minutes.

Comparative Synthetic Example 5

151.51 g of pure water was added to 5.00 g of acid phosphoxy ethyl methacrylate (Product name; Phosmer M, available from Unichemical Co., Ltd., a non-volatile component by the dryness method at 100° C. for 1 hour: 91.8%, a mixture of acid phosphoxy ethyl methacrylate (44.2% by mass), bis[2-(methacryloyloxy)ethyl]phosphate (28.6% by mass) and other substances (27.2% by mass)) and sufficiently dissolved, then, 16.83 g of ethanol, 3.82 g of 2-(dimethylamino)ethyl methacrylate (available from Tokyo Chemical Industry Co., Ltd.) and 0.04 g of 2,2'-azobis[N-(2-carboxyethyl)-2-methylpropionamidine] (Product name; VA-057, available from Wako Pure Chemical Industries, Ltd.) were added thereto while maintaining at 20° C. or lower and stirred to mix uniformly. The mixed solution was charged into a flask equipped with a condenser, this was subjected to nitrogen flow, and raised to a reflux temperature while stirring over 0.5 hour, then, it became a gelled solid within 10 minutes after reflux.

Preparation of Composition for Forming Coating Film (A) using Varnish Containing Copolymer Obtained in Synthetic Example 1

To 1.00 g of the varnish containing a copolymer obtained in the above-mentioned Synthetic example 1 were added 0.90 g of pure water and 0.10 g of ethanol and the mixture was sufficiently stirred to prepare a composition (A) for forming a coating film.
(Preparation of Silicon Wafer)
Commercially available silicon wafer for evaluating a semiconductor was used as such.
(Preparation of Glass Substrate (G) for Platelet Adhesion Experiment)
A glass substrate (TEMPAX Float [Registered Trademark]φ=12 mm) was washed with a UV/ozone cleaning apparatus (UV253E, manufactured by Filgen Inc.) for 10 minutes to clean the surface to obtain a glass substrate (G).

Example 1

The above-mentioned composition (A) for forming a coating film was spin coated on a silicon wafer or the above-mentioned glass substrate (G), and dried in an oven at 45° C. for 12 hours. Thereafter, the uncured composition for forming a film attached onto the coating film was washed in pure water with ultrasonic wave for 5 minutes, and further thoroughly washed with PBS and pure water to obtain a silicon wafer or a glass substrate onto which the coating film has been formed. By using the above-mentioned silicon wafer, when a film thickness of the coating film was confirmed by an optical interference film thickness meter, then, it was 25 Å.

Example 2

To 1.00 g of the varnish containing a copolymer obtained in the above-mentioned Synthetic example 2 was added 2.00 g of pure water and the mixture was thoroughly stirred to prepare a composition for forming a coating film. By using the obtained composition for forming a coating film, a silicon wafer or a glass substrate onto which a coating film has been formed was obtained in the same manner as in Example 1. By using the above-mentioned silicon wafer, when a film thickness of the coating film was confirmed by an optical interference film thickness meter, then, it was 21 Å.

Example 3

To 1.00 g of the varnish containing a copolymer obtained in the above-mentioned Synthetic example 3 was added 2.00 g of PBS and the mixture was thoroughly stirred to prepare a composition for forming a coating film. By using the obtained composition for forming a coating film, a silicon wafer or a glass substrate onto which a coating film has been formed was obtained in the same manner as in Example 1. By using the above-mentioned silicon wafer, when a film thickness of the coating film was confirmed by an optical interference film thickness meter, then, it was 12 Å.

Example 4

A silicon wafer or the above-mentioned glass substrate (G) was dipped in the above-mentioned composition (A) for forming a coating film for 24 hours and after removing the excess composition with an Air brush, then, baked in an oven at 45° C. for 12 hours as a drying process. Thereafter, as a washing process, the excessively attached uncured composition for forming a coating film was washed in pure water by ultrasonic wave for 5 minutes, and thoroughly washed with PBS and pure water to obtain a silicon wafer or a glass substrate onto which a coating film has been formed. By using the above-mentioned silicon wafer, when a film thickness of the coating film was confirmed by an optical interference film thickness meter, then, it was 21 Å.

Example 5

A silicon wafer or the above-mentioned glass substrate (G) was dipped in the above-mentioned composition (A) for forming a coating film for 24 hours and after removing the excessive composition with an Air brush, as a drying process, it was allowed to stand under an environment of at room temperature of 25° C. and a humidity of 40% for 24 hours. Thereafter, as a washing process, the excessively attached uncured composition for forming a coating film was washed in pure water by ultrasonic wave for 5 minutes, and thoroughly washed with PBS and pure water to obtain a silicon wafer or a glass substrate onto which a coating film has been formed. By using the above-mentioned silicon wafer, when a film thickness of the coating film was confirmed by an optical interference film thickness meter, then, it was 22 Å.

Example 6

A silicon wafer or a glass substrate which a coating film has been formed was obtained in the same manner as in Example 1 except for changing the drying temperature to 150° C. and the drying time to 0.5 hour by a hot plate. By using the above-mentioned silicon wafer, when a film thickness of the coating film was confirmed by an optical interference film thickness meter, then, it was 62 Å.

Example 7

A coating film formed onto a silicon wafer or a polystyrene (PS) substrate was obtained in the same manner as in Example 1 except for changing the above-mentioned glass substrate (G) of Example 1 to the following PS substrate. By using the above-mentioned silicon wafer, when a film thickness of the coating film was confirmed by an optical interference film thickness meter, then, it was 25 Å.

(Preparation of PS Substrate)

In 0.99 g of toluene was dissolved 0.01 g of polystyrene (average molecular weight: 35,000) (available from Aldrich Co.) and stirred until the mixture became transparent to prepare a PS solution. The above-mentioned PS solution was spin coated onto the above-mentioned glass substrate (G), and baked by a hot plate at 150° C. for 5 minutes to prepare a PES substrate.

Example 8

A coating film formed onto a silicon wafer or a polyether sulfone (PES) substrate was obtained in the same manner as in Example 1 except for changing the above-mentioned glass substrate (G) of Example 1 to the following PES substrate. By using the above-mentioned silicon wafer, when a film thickness of the coating film was confirmed by an optical interference film thickness meter, then, it was 25 Å.

(Preparation of PES Substrate)

In 0.99 g of 1,1,2,2-tetrachloroethane (available from Tokyo Chemical Industry Co., Ltd.) was dissolved 0.01 g of poly(oxy-1,4-phenylenesulfonyl-1,4-phenylene) (available from Aldrich Co.) and stirred until the mixture became transparent to prepare a PES solution. The above-mentioned PES solution was spin coated onto the above-mentioned glass substrate (G), and baked by a hot plate at 200° C. for 5 minutes to prepare a PES substrate.

(PES Film)

A film (about 0.1 mm) of a commercially available polyether sulfone (PES) prepared by the bar coating method was cut to about 1 cm square was made a PES film.

(Polyethylene (PE) Resin Substrate, Polypropylene (PP) Resin Substrate, Polyethylene Terephthalate (PET) Resin Substrate and Polytetrafluoroethylene (PTFE) Resin Substrate)

Various kinds of substrates purchased from CUTPLA-.COM (http://www.cutpla.com/) were used.

Example 9

The quartz resonator (Q-Sense, QSX304) onto which $SiO_2$ has been deposited was washed by using a UV/ozone cleaning apparatus (UV253E, manufactured by Filgen Inc.) for 10 minutes. The above-mentioned composition (A) for forming a coating film was spin coated thereon, and as a drying process, baked in an oven at 45° C. for 12 hours. Thereafter, as a washing process, the excessively attached uncured composition for forming a coating film was washed in pure water by ultrasonic wave for 5 minutes, and further thoroughly washed with PBS and pure water to obtain a surface treated QCM sensor ($SiO_2$).

Example 10

The above-mentioned composition (A) for forming a coating film was spin coated onto each of three sheets of silicon wafers, and dried on a hot plate at 50° C. for 10 minutes, 12 hours and 24 hour, respectively. Thereafter, the uncured composition for forming a film attached onto the coating film was washed in pure water by ultrasonic wave for 5 minutes, and further thoroughly washed with PBS and pure water to obtain a silicon wafer onto which the coating film has been formed. By using the above-mentioned silicon wafer, when a film thickness of the coating film was confirmed by an optical interference film thickness meter, then, it was 22 Å with a drying time of 10 minutes, 21 Å with a drying time of 12 hours, and 36 Å with a drying time of 24 hours.

Example 11

The above-mentioned composition (A) for forming a coating film was spin coated onto each of two sheets of silicon wafers, and dried on a hot plate at 100° C. for 10 minutes and 12 hours, respectively. Thereafter, the uncured composition for forming a film attached onto the coating film was washed in pure water by ultrasonic wave for 5 minutes, and further thoroughly washed with PBS and pure water to obtain a silicon wafer onto which the coating film has been formed. By using the above-mentioned silicon wafer, when a film thickness of the coating film was confirmed by an optical interference film thickness meter, then, it was 30 Å with the drying time of 10 minutes and 89 Å with the drying time of 12 hours.

Example 12

The above-mentioned composition (A) for forming a coating film was spin coated onto a silicon wafer, and dried on a hot plate at 200° C. for 10 minutes. Thereafter, the uncured composition for forming a film attached onto the coating film was washed in pure water by ultrasonic wave for 5 minutes, and further thoroughly washed with PBS and pure water to obtain a silicon wafer onto which the coating film has been formed. By using the above-mentioned silicon wafer, when a film thickness of the coating film was confirmed by an optical interference film thickness meter, then, it was 145 Å.

Example 13

The above-mentioned composition (A) for forming a coating film was spin coated onto each of two sheets of the above-mentioned PES substrates, and dried on a hot plate at 50° C. for 12 hours and 24 hours, respectively. Thereafter, the uncured composition for forming a film attached onto the coating film was washed in pure water by ultrasonic wave for 5 minutes, and further thoroughly washed with PBS and pure water to obtain a PES substrate onto which the coating film has been formed. By using the above-mentioned PES substrate, when a film thickness of the coating film was confirmed by an optical interference film thickness meter, then, it was 29 Å with the drying time of 12 hours and 29 Å with the drying time of 24 hours.

(Preparation of QCM Sensor (PES))

The quartz resonator (Q-Sense, QSX304) onto which Au has been deposited was washed by using a UV/ozone cleaning apparatus (UV253E, manufactured by Filgen Inc.) for 10 minutes, and immediately after dipped in 100 ml of an ethanol solution into which 0.1012 g of 1-decanethiol (available from Tokyo Chemical Industry Co., Ltd.) for 24 hours. After washing the surface of the sensor with ethanol, it was naturally dried, and a varnish in which 1.00 g of poly(oxy-1,4-phenylenesulfonyl-1,4-phenylene) (available from Aldrich Co.) has been dissolved in 99.00 g of 1,1,2,2-tetrachloroethane was spin coated on a film sensor side by a spin coater with 3,500 rpm/30 sec and dried at 205° C./1 min to prepare a QCM sensor (PES).

Example 14

To 1.00 g of the varnish containing a copolymer obtained in the above-mentioned Synthetic example 5 were added 5.10 g of pure water and 0.57 g of ethanol, and the mixture was thoroughly stirred to prepare a composition for forming a coating film. The above-mentioned PES film, silicon wafer or the above-mentioned glass substrate (G) was dipped in the obtained composition for forming a coating film, and dried in an oven at 45° C. for 12 hours. Thereafter, the uncured composition for forming a film attached onto the coating film was thoroughly washed with PBS and pure water to obtain a silicon wafer, a PES film or a glass substrate onto which the coating film has been formed. By using the above-mentioned silicon wafer, when a film thickness of the coating film was confirmed by an optical interference film thickness meter, then, it was 65 Å. Also, the above-mentioned composition for forming a coating film was spin coated onto a QCM sensor (PES) with 3,500 rpm/30 sec, and as a drying process, based in an oven at 45° C. for 12 hours. Thereafter, as a washing process, the excessively attached uncured composition for forming a coating film was washed with PBS and ultrapure water each twice to make a surface treated QCM sensor (PES).

Example 15

To 1.00 g of the varnish containing a copolymer obtained in the above-mentioned Synthetic example 6 were added 7.27 g of pure water and 3.39 g of ethanol, and the mixture was thoroughly stirred to prepare a composition for forming a coating film. In the same manner as in Example 14, a silicon wafer, a glass substrate, a PES film, a polyethylene (PE) resin substrate, a polypropylene (PP) resin substrate, a polyethylene terephthalate (PET) resin substrate, a polytetrafluoroethylene (PTFE) resin substrate or a surface treated QCM sensor (PES) onto each of which a coating film has been formed was obtained. By using the above-mentioned silicon wafer, when a film thickness of the coating film was confirmed by an optical interference film thickness meter, then, it was 44 Å.

Example 16

To 1.00 g of the varnish containing a copolymer obtained in the above-mentioned Synthetic example 7 were added 10.78 g of pure water and 4.89 g of ethanol, and the mixture was thoroughly stirred to prepare a composition for forming a coating film. In the same manner as in Example 14, a silicon wafer, a glass substrate or a PES film onto which a coating film has been formed was obtained. By using the above-mentioned silicon wafer, when a film thickness of the coating film was confirmed by an optical interference film thickness meter, then, it was 59 Å.

Example 17

To 1.00 g of the varnish containing a copolymer obtained in the above-mentioned Synthetic example 8 were added 13.11 g of pure water and 5.89 g of ethanol, and the mixture was thoroughly stirred to prepare a composition for forming a coating film. In the same manner as in Example 14, a silicon wafer, a glass substrate or a PES film onto which a coating film has been formed was obtained. By using the above-mentioned silicon wafer, when a film thickness of the coating film was confirmed by an optical interference film thickness meter, then, it was 62 Å.

Example 18

To 1.00 g of the varnish containing a copolymer obtained in the above-mentioned Synthetic example 9 were added 8.44 g of pure water and 3.89 g of ethanol, and the mixture was thoroughly stirred to prepare a composition for forming a coating film. In the same manner as in Example 14, a silicon wafer, a glass substrate or a PES film onto which a coating film has been formed was obtained. By using the above-mentioned silicon wafer, when a film thickness of the coating film was confirmed by an optical interference film thickness meter, then, it was 55 Å.

Example 19

To 1.00 g of the varnish containing a copolymer obtained in the above-mentioned Synthetic example 10 were added 14.35 g of pure water and 0.90 g of ethanol, and the mixture was thoroughly stirred to prepare a composition for forming a coating film. In the same manner as in Example 14, a silicon wafer, a glass substrate or a PES film onto which a coating film has been formed was obtained. By using the above-mentioned silicon wafer, when a film thickness of the coating film was confirmed by an optical interference film thickness meter, then, it was 13 Å.

Example 20

To 1.00 g of the varnish containing a copolymer obtained in the above-mentioned Synthetic example 11 were added 11.10 g of pure water and 1.23 g of ethanol, and the mixture was thoroughly stirred to prepare a composition for forming a coating film. In the same manner as in Example 14, a silicon wafer, a glass substrate, a PES film or a surface treated QCM sensor (PES) onto which a coating film has been formed was obtained. By using the above-mentioned silicon wafer, when a film thickness of the coating film was confirmed by an optical interference film thickness meter, then, it was 68 Å.

Example 21

To 1.00 g of the varnish containing a copolymer obtained in the above-mentioned Synthetic example 12 were added 8.44 g of pure water and 3.89 g of ethanol, and the mixture was thoroughly stirred to prepare a composition for forming a coating film. In the same manner as in Example 14, a silicon wafer, a glass substrate or a PBS film onto which a coating film has been formed was obtained. By using the above-mentioned silicon wafer, when a film thickness of the coating film was confirmed by an optical interference film thickness meter, then, it was 49 Å.

Example 22

To 1.00 g of the varnish containing a copolymer obtained in the above-mentioned Synthetic example 13 were added 8.44 g of pure water and 3.89 g of ethanol, and the mixture was thoroughly stirred to prepare a composition for forming a coating film. In the same manner as in Example 14, a silicon wafer, a PES film or a glass substrate onto which a coating film has been formed was obtained. By using the above-mentioned silicon wafer, when a film thickness of the coating film was confirmed by an optical interference film thickness meter; then, it was 49 Å.

Example 23

To 1.00 g of the varnish containing a copolymer obtained in the above-mentioned Synthetic example 14 were added 8.44 g of pure water and 3.89 g of ethanol, and the mixture was thoroughly stirred to prepare a composition for forming a coating film. In the same manner as in Example 14, a silicon wafer, a glass substrate or a PES film onto which a coating film has been formed was obtained. By using the above-mentioned silicon wafer, when a film thickness of the coating film was confirmed by an optical interference film thickness meter, then, it was 50 Å.

Example 24

To 1.00 g of the varnish containing a copolymer obtained in the above-mentioned Synthetic example 15 were added 8.44 g of pure water and 3.89 g of ethanol, and the mixture was thoroughly stirred to prepare a composition for forming a coating film. In the same manner as in Example 14, a silicon wafer, a glass substrate or a PES film onto which a coating film has been formed was obtained. By using the above-mentioned silicon wafer, when a film thickness of the coating film was confirmed by an optical interference film thickness meter, then, it was 22 Å.

Example 25

To 1.00 g of the varnish containing a copolymer obtained in the above-mentioned Synthetic example 16 were added 8.44 g of pure water and 3.89 g of ethanol, and the mixture was thoroughly stirred to prepare a composition for forming a coating film. In the same manner as in Example 14, a silicon wafer, a glass substrate or a PES film onto which a coating film has been formed was obtained. By using the above-mentioned silicon wafer, when a film thickness of the coating film was confirmed by an optical interference film thickness meter, then, it was 22 Å.

Example 26

To 1.00 g of the varnish containing a copolymer obtained in the above-mentioned Synthetic example 6 were added 4.85 g of pure water, 5.72 g of ethanol and 0.095 g of 1 mol/L aqueous ammonia, and the mixture was thoroughly stirred to prepare a composition for forming a coating film. In the same manner as in Example 14, a silicon wafer, a glass substrate or a PES film onto which a coating film has been formed was obtained. By using the above-mentioned silicon wafer, when a film thickness of the coating film was confirmed by an optical interference film thickness meter, then, it was 39 Å.

Example 27

To 1.00 g of the varnish containing a copolymer obtained in the above-mentioned Synthetic example 6 were added 4.95 g of pure water, 5.72 g of ethanol and 0.02 g of diethanolamine (available from Tokyo Chemical Industry Co., Ltd.), and the mixture was thoroughly stirred to prepare a composition for forming a coating film. In the same manner as in Example 14, a silicon wafer, a glass substrate, a PES film or a surface treated QCM sensor (PES) onto which a coating film has been formed was obtained. By using the above-mentioned silicon wafer, when a film thickness of the coating film was confirmed by an optical interference film thickness meter, then, it was 45 Å.

Example 28

To 1.00 g of the varnish containing a copolymer obtained in the above-mentioned Synthetic example 6 were added 0.06 g of pure water, 10.60 g of ethanol and 0.02 g of diethanolamine (available from Tokyo Chemical Industry Co., Ltd.), and the mixture was thoroughly stirred to prepare a composition for forming a coating film. In the same manner as in Example 14, a silicon wafer, a glass substrate, a PES film or a surface treated QCM sensor (PES) onto which a coating film has been formed was obtained. By using the above-mentioned silicon wafer, when a film thickness of the coating film was confirmed by an optical interference film thickness meter, then, it was 68 Å.

Example 29

To 1.00 g of the varnish containing a copolymer obtained in the above-mentioned Synthetic example 6 were added 0.02 g of pure water, 10.60 g of ethanol and 0.07 g of choline (48-50% aqueous solution) (available from Tokyo Chemical Industry Co., Ltd.), and the mixture was thoroughly stirred to prepare a composition for forming a coating film. In the same manner as in Example 14, a silicon wafer, a glass substrate, a PES film or a surface treated QCM sensor (PES) onto which a coating film has been formed was obtained. By using the above-mentioned silicon wafer, when a film thickness of the coating film was confirmed by an optical interference film thickness meter, then, it was 122 Å.

Example 30

To 1.00 g of the varnish containing a copolymer obtained in the above-mentioned Synthetic example 6 were added 4.99 g of pure water, 5.74 g of ethanol and 0.05 g of sodium hydroxide, and the mixture was thoroughly stirred to prepare a composition for forming a coating film. In the same manner as in Example 14, a silicon wafer, a glass substrate or a PES film onto which a coating film has been formed was obtained. By using the above-mentioned silicon wafer, when a film thickness of the coating film was confirmed by an optical interference film thickness meter, then, it was 38 Å.

Example 31

To 1.00 g of the varnish containing a copolymer obtained in the above-mentioned Synthetic example 6 were added 4.01 g of pure water, 5.72 g of ethanol and 0.95 g of 1 mol/L aqueous ammonia, and the mixture was thoroughly stirred to prepare a composition for forming a coating film. In the same manner as in Example 14, a silicon wafer, a glass substrate, a PES film or a surface treated QCM sensor (PES) onto which a coating film has been formed was obtained. By using the above-mentioned silicon wafer, when a film thickness of the coating film was confirmed by an optical interference film thickness meter, then, it was 40 Å.

Example 32

To 1.00 g of the varnish containing a copolymer obtained in the above-mentioned Synthetic example 6 were added 7.27 g of PBS and 3.39 g of ethanol, and the mixture was thoroughly stirred to prepare a composition for forming a coating film. In the same manner as in Example 14, a silicon wafer, a glass substrate or a PES film onto which a coating film has been formed was obtained. By using the above-mentioned silicon wafer, when a film thickness of the coating film was confirmed by an optical interference film thickness meter, then, it was 55 Å.

Example 33

To 1.00 g of the varnish containing a copolymer obtained in the above-mentioned Synthetic example 17 were added 22.45 g of pure water and 9.88 g of ethanol, and the mixture was thoroughly stirred to prepare a composition for forming a coating film. In the same manner as in Example 14, a silicon wafer, a glass substrate or a PES film onto which a coating film has been formed was obtained. By using the above-mentioned silicon wafer, when a film thickness of the coating film was confirmed by an optical interference film thickness meter, then, it was 79 Å.

Example 34

To 1.00 g of the varnish containing a copolymer obtained in the above-mentioned Synthetic example 18 were added 10.78 g of pure water and 4.89 g of ethanol, and the mixture was thoroughly stirred to prepare a composition for forming a coating film. In the same manner as in Example 14, a silicon wafer, a glass substrate or a PES film onto which a coating film has been formed was obtained. By using the above-mentioned silicon wafer, when a film thickness of the coating film was confirmed by an optical interference film thickness meter, then, it was 28 Å.

Example 35

To 1.00 g of the varnish containing a copolymer obtained in the above-mentioned Synthetic example 19 were added 10.78 g of pure water and 4.89 g of ethanol, and the mixture was thoroughly stirred to prepare a composition for forming a coating film. In the same manner as in Example 14, a silicon wafer, a glass substrate or a PES film onto which a coating film has been formed was obtained. By using the above-mentioned silicon wafer, when a film thickness of the coating film was confirmed by an optical interference film thickness meter, then, it was 82 Å.

Example 36

To 1.00 g of the varnish containing a copolymer obtained in the above-mentioned Synthetic example 20 were added 22.45 g of pure water and 9.88 g of ethanol, and the mixture was thoroughly stirred to prepare a composition for forming a coating film. In the same manner as in Example 14, a silicon wafer, a glass substrate or a PES film onto which a coating film has been formed was obtained. By using the above-mentioned silicon wafer, when a film thickness of the coating film was confirmed by an optical interference film thickness meter, then, it was 11 Å.

Comparative Example 1

To 1.00 g of the polymerized solution obtained in the above-mentioned Comparative synthetic example 1 were added 1.80 g of pure water and 0.20 g of ethanol and the mixture was thoroughly stirred to obtain a composition for forming a coating film. A glass substrate or a silicon wafer was obtained by treating the obtained composition for forming a coating film in the same manner as in Example 1. When a film thickness of the above-mentioned silicon wafer was confirmed by an optical interference film thickness meter, then, no coating film was found to be formed (film thickness: 0 Å).

Comparative Example 2

A silicon wafer or a glass substrate was obtained by using the above-mentioned composition (A) for forming a coating film and treating it in the same manner as in Example 4 except for carrying out the drying process. When a film thickness of the above-mentioned silicon wafer was confirmed by an optical interference film thickness meter, then, no coating film was found to be formed (film thickness: 0 Å).

Comparative Example 3

In the same manner as in Example 1 except for the drying temperature of 205° C. and the drying time of 12 hours, a coating film formed onto a silicon wafer or a glass substrate was obtained. When a film thickness of the coating film was confirmed by an optical interference film thickness meter, then, it was 78 Å.

Comparative Example 4

In the same manner as in Example 1 except for not using the composition for forming a coating film, a glass substrate was obtained.

Comparative Example 5

In the same manner as in Example 7 except for not using the composition for forming a coating film, a PS substrate was obtained.

Comparative Example 6

In the same manner as in Example 8 except for not using the composition for forming a coating film, a PES substrate was obtained.

Comparative Example 7

In the same manner as in Example 9 except for subjecting to the drying process, a surface treated QCM sensor was obtained.

Comparative Example 8

In the same manner as in Example 9 except for not forming a film by the composition for forming a coating film, a surface treated QCM sensor was obtained.

Comparative Example 9

A PES film, a polyethylene (PE) resin substrate, a polypropylene (PP) resin substrate, a polyethylene terephthalate (PET) resin substrate, a polytetrafluoroethylene (PTFE) resin substrate, or the above-mentioned QCM sensor (PES) was dried in an oven at 45° C. for 12 hours. Thereafter, they were further thoroughly washed with PBS and pure water to obtain a PES film, a polyethylene (PE) resin substrate, a polypropylene (PP) resin substrate, a polyethylene terephthalate (PET) resin substrate, a polytetrafluoroethylene (PTFE) resin substrate or a surface treated QCM sensor (PES).

Comparative Example 10

To 1.00 g of the polymerized solution obtained in the above-mentioned Comparative synthetic example 1 were added 1.80 g of pure water and 0.20 g of ethanol and the mixture was thoroughly stirred to obtain a composition for forming a coating film. The above-mentioned PES film, a silicon wafer or the above-mentioned glass substrate (G) was dipped in the obtained composition for forming a coating film, and dried in an oven at 45° C. for 12 hours. Thereafter, the uncured composition for forming a film attached onto the coating film was thoroughly washed with PBS and pure water to obtain a silicon wafer, a glass substrate or a PES film onto which the coating film has been formed. By using the above-mentioned silicon wafer, when a film thickness was confirmed by an optical interference film thickness meter, then, no coating film was found to be formed (film thickness: 0 Å).

Also, the above-mentioned composition for forming a coating film was spin coated onto a QCM sensor (PES) with 3,500 rpm/30 sec, and as a drying process, it was baked in an oven at 45° C. for 12 hours. Thereafter, as a washing process, the excessively attached uncured composition for forming a coating film was washed with PBS and ultrapure water each twice to make a surface treated QCM sensor (PES).

Comparative Example 11

To 1.00 g of polyvinylpyrrolidone (K90) (available from Tokyo Chemical Industry Co., Ltd.) were added 59.40 g of pure water and 39.60 g of ethanol, and the mixture was thoroughly stirred to prepare a composition for faulting a coating film. The above-mentioned PES film, a silicon wafer or the above-mentioned glass substrate (G) was dipped in the obtained composition for forming a coating film, and dried in an oven at 45° C. for 12 hours. Thereafter, the uncured composition for forming a film attached onto the coating film was thoroughly washed with PBS and pure water to obtain a silicon wafer, a glass substrate or a PES film onto which the coating film has been formed. By using the above-mentioned silicon wafer, when a film thickness of the coating film was confirmed by an optical interference film thickness meter, then, no coating film was found to be formed (film thickness: 22 Å).

Also, the above-mentioned composition for forming a coating film was spin coated onto a QCM sensor (PES) with 3,500 rpm/30 sec, and as a drying process, it was baked in an oven at 45° C. for 12 hours. Thereafter, as a washing process, the excessively attached uncured composition for forming a coating film was thoroughly washed with PBS and ultrapure water each twice to make a surface treated QCM sensor (PES).

[Platelet Adhesion Test]
(Preparation of Platelet Solution)

To 0.5 mL of a 3.8% by mass sodium citrate solution was mixed 4.5 mL of blood collected from a healthy volunteer, platelet-rich plasma (PRP) at an upper layer was recovered by centrifugal separation [Refrigerated Centrifuge 5900 (manufactured by Kubota Corporation), at 1,000 rpm/10 min and room temperature]. Subsequently, centrifugal separation (the above-mentioned Centrifuge, 3500 rpm/10 min, room temperature) of a lower layer was performed to recover platelet-poor plasma (PPP) at an upper layer. A number of the platelets of the PRP was counted by a multi-item automatic Hematology Analyzer (XT-2000i, manufactured by Sysmex Corporation), and a platelet concentration of the PRP was adjusted to be $30 \times 10^4$ cells/μL by using the PPP.

(Platelet Adhesion Test)

Glass substrates, PS substrates, PES substrates, PP resin substrates, PET resin substrates, PTFE resin substrates or PES films of Examples 1 to 8, Examples 14 to 23, Examples 25 to 35, Comparative examples 1 to 6, Comparative example 9 and Comparative example 10 were provided to 24-well flat bottom microplate (manufactured by Corning Inc.). Into the well of the plate to which these substrates were provided was added 300 μL of the PRP solution which has been adjusted to the above-mentioned platelet concentration. At the state while maintaining at 5% carbon dioxide concentration, these were allowed to stand in a $CO_2$ incubator at 37° C. for 24 hours. After lapsing a predetermined allowing time, the PRP in the plate was removed, and the plate was washed five times with each 3 mL of PBS. Thereafter, 2 mL of a PBS solution containing 2.5% by volume of glutaraldehyde was added thereto, allowed to stand at 4° C. over day and night, then, the PBS solution of glutaraldehyde was removed, and the plate was washed five times with each 3 mL of ultrapure water (Milli-Q water). Further, the plate was washed three times with each 1 mL of 70% ethanol-water (v/v), and air-dried.

[Measurement of Number of Adhered Platelets]

To the glass substrates, the PS substrates, the PES substrates, the PP resin substrates, the PET resin substrates, the PTFE resin substrates or the PES films of Examples 1 to 8, Examples 14 to 23, Examples 25 to 38, Comparative examples 1 to 6, Comparative example 9 and Comparative example 10 which had been subjected to the above-mentioned platelet adhesion test were deposited Pt—Pd for 1 minute by using ion sputter (E-1030, manufactured by Hitachi High Technologies Corporation). Thereafter, adhesion of the platelets was observed by an electron microscope (S-4800, manufactured by Hitachi High Technologies Corporation) with 1,000-fold. Number of the adhered platelets at the five portions from the center portion of the glass substrate within a radius of 2 mm was counted by the electron microscope. By averaging the counted values of the respective portions, it was made a number of adhered platelets. The results are shown in the following Tables 1 to 4.

TABLE 1

| | Number of platelets adhered (number) | | |
|---|---|---|---|
| | Glass | PS | PES |
| Example 1 | 0 | | |
| Example 2 | 2 | | |
| Example 3 | 1 | | |
| Example 4 | 2 | | |
| Example 5 | 1 | | |
| Example 6 | 1 | | |
| Example 7 | | 3 | |
| Example 8 | | | 2 |

TABLE 2

| | Number of platelets adhered (number) | | | | |
|---|---|---|---|---|---|
| | PES | PE | PP | PET | PTFE |
| Example 14 | 2 | | | | |
| Example 15 | 1 | 4 | 2 | 3 | 6 |
| Example 16 | 17 | | | | |
| Example 17 | 31 | | | | |
| Example 18 | 10 | | | | |
| Example 19 | 25 | | | | |
| Example 20 | 6 | | | | |
| Example 21 | 6 | | | | |
| Example 22 | 4 | | | | |
| Example 23 | 0 | | | | |
| Example 25 | 1 | | | | |
| Example 26 | 4 | | | | |
| Example 27 | 2 | | | | |
| Example 28 | 6 | | | | |
| Example 29 | 4 | | | | |
| Example 30 | 6 | | | | |
| Example 31 | 3 | | | | |
| Example 32 | 2 | | | | |
| Example 33 | 10 | | | | |
| Example 34 | 5 | | | | |
| Example 35 | 2 | | | | |

TABLE 3

| | Number of platelets adhered (number) | | |
|---|---|---|---|
| | Glass | PS | PES |
| Comparative Example 1 | 45 | | |
| Comparative Example 2 | 70 | | |
| Comparative Example 3 | 99 | | |

TABLE 3-continued

| | Number of platelets adhered (number) | | |
|---|---|---|---|
| | Glass | PS | PES |
| Comparative Example 4 | 47 | | |
| Comparative Example 5 | | 85 | |
| Comparative Example 6 | | | 69 |

TABLE 4

| | Number of platelets adhered (number) | | | | |
|---|---|---|---|---|---|
| | PES | PE | PP | PET | PTFE |
| Comparative Example 9 | 107 | 17 | 35 | 73 | 53 |
| Comparative Example 10 | 138 | | | | |

(PES: Example 8 and Comparative example 6 are the results on the PES substrates, and Examples 14 to 35 and Comparative examples 9 and 10 are the results on the PES films.)

[Protein Adhesion Test; QCM-D Measurement]

The QCM sensors surface treated in Example 9, Comparative example 7 and Comparative example 8 were attached to a dissipation type quartz resonator microbalance QCM-D (E4, manufactured by Q-Sense Co.), and PBS was flown until a stable base line has been established in which change in the frequency became 1 Hz or less in one hour. Next, the frequency of the stabilized base line was made 0 Hz and PBS was flown for about 10 minutes. Subsequently, a solution in which human serum (available from Aldrich Co.) was diluted to 10% with PBS was flown for about 30 minutes, thereafter PBS was again flown for about 20 minutes, and then, a shift ($\Delta f$) of an adhesion induced frequency at eleventh overtone was read. The measured values are shown in Table 5. In Example 9, the shift value was close to 0, and no human serum was adhered, but in Comparative example 7 and Comparative example 8, as compared to Example 9, it was shown that the human serum component had been adhered.

TABLE 5

| Adhesion induced frequency shift value ($\Delta f$) | |
|---|---|
| Example 9 | −1 |
| Comparative Example 7 | −18 |
| Comparative Example 8 | −33 |

[Protein Adhesion Test; QCM-D Measurement (2)]

The PES sensors surface treated in Examples 14, 15, 20, 27 to 29 and 31, Comparative example 9 and Comparative example 11 were attached to a dissipation type quartz resonator microbalance QCM-D (E4, manufactured by Q-Sense Co.), and PBS was flown until a stable base line has been established in which change in the frequency became 1 Hz or less in one hour. Next, the frequency of the stabilized base line was made 0 Hz and PBS was flown for about 10 minutes. Subsequently, a solution in which fibrinogen, derived from a human plasma (available from Wako Pure Chemical Industries, Ltd.) or fibronectin, derived from a human plasma (available from Sigma-Aldrich Co. LLC.) was diluted to 100 μg/ml with PBS was flown for about 30 minutes, thereafter PBS was again flown for about 20 minutes, and then, a shift ($\Delta f$) of an adhesion induced frequency at eleventh overtone was read. By using Q-Tools (manufactured by Q-Sense Co.) for analysis, a shift ($\Delta f$) of the adhesion induced frequency is converted into a mass (ng/cm$^2$) per unit surface area of a shift ($\Delta$f) of the adhesion induced frequency explained by the Sauerbrey's formula and shown as an adhered amount of the biological substance in Table 6. As compared to Comparative examples, Examples showed adhesion amounts of various proteins with one digit large.

[Table 6]

TABLE 6

| | Mass (ng/cm2) per unit surface area | |
|---|---|---|
| | Fibrinogen | Fibronectin |
| Example 14 | 121 | 15 |
| Example 15 | 186 | 8 |
| Example 20 | 300 | 15 |
| Example 27 | 131 | — |
| Example 28 | 59 | — |
| Example 29 | 58 | — |
| Example 31 | 244 | 16 |
| Comparative Example 9 | 2214 | 837 |
| Comparative Example 11 | 1102 | 34 |

[Measurement of Contact Angle in Liquid]

A contact angle in a liquid of CH$_2$I$_2$ (diiodomethane) in PBS was measured. The measurement results are shown in Table 7.

[Table 7]

TABLE 7

| | Measurement of contact angle in liquid (°) | | | |
|---|---|---|---|---|
| | Substrate | Drying temperature | Drying time 10 min | Drying time 12 hrs | Drying time 24 hrs |
| Example 10 | Silicon | 50° C. | 144 | 145 | 144 |
| Example 11 | Silicon | 100° C. | 142 | 145 | — |
| Example 12 | Silicon | 200° C. | 140 | — | — |
| Example 13 | PES | 50° C. | — | 141 | 142 |

With regard to the uncoated silicon wafer and PES substrate, when a contact angle in liquid was measured in the same conditions to those of Example 10 to Example 13, then, the silicon wafer was 144° and the PES substrate (PES film thickness: 300 Å) was 60°.

From the results as mentioned above, in the surface contact angle measurement method in liquid, a contact angle to the coating film of CH$_2$I$_2$ in PBS is 137° to 151°, more preferably 139° to 149°.

[Measurement of Particle Diameter by Dynamic Light Scattering Method]

Measurements of a sol particle diameter in each of the composition for forming a coating film of Examples 14, 15, 16, 18, 19, 20, 21, 26, 30, 33 and 35 were carried out by using a dynamic light scattering photometer (DLS, manufactured by Otsuka Electronics Co., Ltd., Product name: DLS-8000DLTKY).

TABLE 8

| Average particle diameter (nm) | |
|---|---|
| Example 14 | 79 |
| Example 15 | 35 |
| Example 16 | 42 |
| Example 18 | 34 |
| Example 19 | 12 |
| Example 20 | 115 |

TABLE 8-continued

| Average particle diameter (nm) | |
|---|---|
| Example 21 | 46 |
| Example 26 | 40 |
| Example 30 | 18 |
| Example 33 | 151 |
| Example 35 | 22 |

UTILIZABILITY IN INDUSTRY

The coating film using with an ion complex of the present invention firmly fix to any of the substrates with a simple and easy drying process, and the film has a function of inhibiting adhesion of a biological substance. It can be expected to apply for a coating film inhibiting adhesion of the biological substance to an artificial dialyzer, artificial organs, medical equipments, etc.

The invention claimed is:

1. A coating film obtained by a method comprising
a process of applying a composition for forming a coating film which comprises
a random copolymer comprising a recurring unit containing an organic group of the following formula (a) and a recurring unit containing an organic group of the following formula (b):

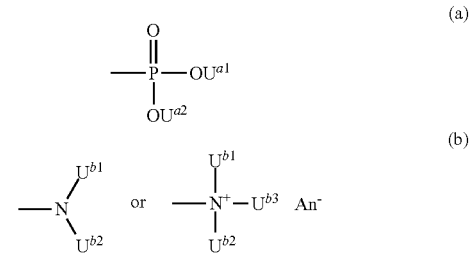

wherein
$U^{a1}$ and $U^{a2}$ each independently represent a hydrogen atom or a linear or branched alkyl group having 1 to 5 carbon atoms,
$U^{b1}$, $U^{b2}$, and $U^{b3}$ are the same and each represent a hydrogen atom, a methyl group, or an ethyl group,
An$^-$ represents an anion selected from the group consisting of a halide ion, an inorganic acid ion, a hydroxide ion and an isothiocyanate ion, and
the recurring unit containing an organic group of the formula (a) in the random copolymer is 20 mol % to 80 mol % relative to the random copolymer, and
a solvent onto a substrate, wherein the composition for forming a coating film is adjusted to a pH of 3.5 to 8.5 by adding a pH adjusting agent prior to applying the composition for forming a coating film onto the substrate; and
a process of drying the coating composition at a temperature of −200° C. to 150° C. to form the coating film, wherein the thickness of the coating film is 10 to 1,000 Å, and
wherein the film has a function of inhibiting adhesion of a biological substance.

2. The coating film according to claim 1, wherein the solvent comprises water or an alcohol.

3. The coating film according to claim 1, wherein a concentration of the random copolymer in the composition for forming a coating film is 0.01% by mass to 4% by mass.

4. The coating film according to claim 1, wherein the substrate is selected from the group consisting of glass, a metal containing compound, a semi-metal containing compound and a resin.

5. The coating film according to claim 1, wherein the random copolymer comprises recurring units of the following formula (a1) and the formula (b1):

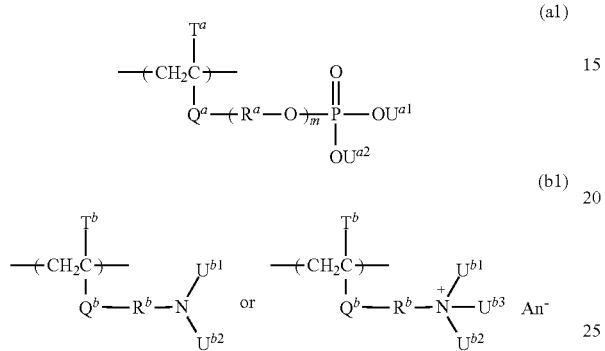

wherein $T^a$, $T^b$, $U^{a1}$, and $U^{a2}$ each independently represent a hydrogen atom or a linear or branched alkyl group having 1 to 5 carbon atoms, $U^{b1}$, $U^{b2}$, and $U^{b3}$ are the same and each represent a hydrogen atom, a methyl group, or an ethyl group, $Q^a$ and $Q^b$ each independently represent a single bond, an ester bond or an amide bond, $R^a$ and $R^b$ each independently represent a linear or branched alkylene group having 1 to 10 carbon atoms which may be substituted by a halogen atom, An⁻ represents an anion selected from the group consisting of a halide ion, an inorganic acid ion, a hydroxide ion and an isothiocyanate ion, and m is an integer of 0 to 6.

6. The coating film according to claim 5, wherein m is 1, and $R^a$ and $R^b$ each independently represent an ethylene group or a propylene group.

7. The coating film according to claim 1, wherein the method further comprises a process of washing a film obtained after the process of drying with an aqueous solution containing an electrolyte.

8. A method for manufacturing a coating film comprising a process of applying a composition for forming a coating film which comprises
a random copolymer comprising a recurring unit containing an organic group of the following formula (a) and a recurring unit containing an organic group of the following formula (b):

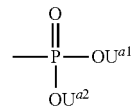

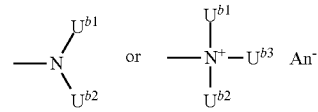

wherein $U^{a1}$ and $U^{a2}$ each independently represent a hydrogen atom or a linear or branched alkyl group having 1 to 5 carbon atoms, $U^{b1}$, $U^{b2}$, and $U^{b3}$ are the same and each represent a hydrogen atom, a methyl group, or an ethyl group, An⁻ represents an anion selected from the group consisting of a halide ion, an inorganic acid ion, a hydroxide ion and an isothiocyanate ion, and wherein the recurring unit containing an organic group of the formula (a) in the random copolymer is 20 mol % to 80 mol % relative to the random copolymer, and a solvent onto a substrate, wherein the composition for forming a coating film is adjusted to a pH of 3.5 to 8.5 by adding a pH adjusting agent prior to applying the composition for forming a coating film onto the substrate; and a process of drying the composition at a temperature of −200° C. to 150° C. to form the coating film, wherein the thickness of the coating film is 10 to 1,000 Å.

9. The coating film according to claim 1, wherein $U^{a1}$ and $U^{a2}$ each represent a hydrogen atom.

10. The coating film according to claim 5, wherein $U^{a1}$ and $U^{a2}$ each represent a hydrogen atom.

11. The coating film according to claim 1, wherein the pH adjusting agent is an organic amine, an alkali metal hydroxide, an alkali metal halide, an inorganic acid, a quaternary ammonium cation, or a mixture thereof.

12. The coating film according to claim 1, wherein the pH adjusting agent is ammonia, diethanolamine, pyridine, N-methyl-D-glucamine, tris(hydroxymethyl)aminomethane, potassium hydroxide, sodium hydroxide, potassium chloride, sodium chloride, sulfuric acid, phosphoric acid, hydrochloric acid, carbonic acid or an alkali metal salt thereof, choline, or a mixture thereof.

13. The coating film according to claim 1, wherein the composition for forming a coating film is adjusted to a pH of 4 to 8 by adding a pH adjusting agent prior to applying the composition for forming a coating film onto the substrate.

* * * * *